(12) United States Patent
Angel

(10) Patent No.: US 9,139,458 B2
(45) Date of Patent: Sep. 22, 2015

(54) COMPOSITIONS AND METHODS OF USE

(71) Applicant: Janet Angel, Lake Forest, IL (US)

(72) Inventor: Janet Angel, Lake Forest, IL (US)

(*) Notice: Subject to any disclaimer, the term of this patent is extended or adjusted under 35 U.S.C. 154(b) by 6 days.

(21) Appl. No.: 13/948,669

(22) Filed: Jul. 23, 2013

(65) Prior Publication Data

US 2014/0273150 A1 Sep. 18, 2014

Related U.S. Application Data

(60) Provisional application No. 61/788,424, filed on Mar. 15, 2013.

(51) Int. Cl.

| | | |
|---|---|---|
| *C12N 9/94* | (2006.01) | |
| *C02F 3/34* | (2006.01) | |
| *B09C 1/10* | (2006.01) | |
| *B09C 1/00* | (2006.01) | |
| *B09C 1/08* | (2006.01) | |
| *C02F 3/32* | (2006.01) | |
| *C02F 101/32* | (2006.01) | |
| *C02F 103/00* | (2006.01) | |
| *C02F 103/08* | (2006.01) | |

(52) U.S. Cl.
CPC . *C02F 3/342* (2013.01); *B09C 1/00* (2013.01); *B09C 1/08* (2013.01); *B09C 1/10* (2013.01); *C02F 3/344* (2013.01); *C12N 9/94* (2013.01); *B09C 2101/00* (2013.01); *C02F 3/322* (2013.01); *C02F 2101/32* (2013.01); *C02F 2103/007* (2013.01); *C02F 2103/08* (2013.01); *C02F 2305/04* (2013.01); *C02F 2305/06* (2013.01)

(58) Field of Classification Search
None
See application file for complete search history.

(56) References Cited

U.S. PATENT DOCUMENTS

| | | | |
|---|---|---|---|
| 3,332,880 A | | 7/1967 | Kessler |
| 3,717,630 A | | 2/1973 | Booth |
| 4,111,855 A | | 9/1978 | Barrat |
| 4,284,435 A | | 8/1981 | Fox |
| 4,415,661 A | | 11/1983 | Thirumalachar |
| 4,865,773 A | | 9/1989 | Kim |
| 5,399,350 A | | 3/1995 | Potter |
| 5,464,766 A | * | 11/1995 | Bruno ................... 435/187 |
| 5,624,684 A | | 4/1997 | Fuisz |
| 5,872,091 A | * | 2/1999 | Cuperus et al. ......... 510/300 |
| 6,458,343 B1 | | 10/2002 | Zeman |
| 8,734,646 B1 | * | 5/2014 | Schuh et al. ............ 210/602 |
| 2001/0019030 A1 | | 9/2001 | Satyanarayana |
| 2005/0173340 A1 | | 8/2005 | Tanaka et al. |
| 2007/0060477 A1 | | 3/2007 | Pedersen |
| 2010/0093063 A1 | | 4/2010 | Scalzi |
| 2011/0281321 A1 | | 11/2011 | Skillicorn |
| 2012/0083412 A1 | | 4/2012 | Trevino |

FOREIGN PATENT DOCUMENTS

| | | |
|---|---|---|
| EP | 0130756 A1 | 1/1985 |
| WO | WO9425580 A1 | 11/1994 |
| WO | WO02094973 A1 | 11/2002 |

OTHER PUBLICATIONS

Wang et al "Potential Approaches to Improving Biodegradation of Hydrocarbons for Bioremediation of Crude Oil Pollution" Journal of Environmental Protection, 2011, 2, 47-55.*
Naggar et al "Bioremediation of Paraffinic and Polynuclear aromatic hydrocarbons Using Laser irradiated Bacillus amyloliquefaciens" Journal of American Science 2010 6(10) 661-670.*
Toledo et al. "Selection and identification of bacteria isolated from waste crude oil with polycyclic aromatic hydrocarbons removal capacities"Systematic and Applied Microbiology 29 (2006) 244-252.*
Jyothi et al. "Identification and Isolation of Hydrocarbon Degrading Bacteria by Molecular Characterization" Helix vol. 2:105-111 (2012).*
Nieuwenhuyzen "Lecithin production and properties"J. Am. Oil Chemists' Soc., 1976 (53) 425-427.*
Ayyachamy et al. "Production and partial characterization of cellulase free xylanase by Bacillus subtilis C 01 using agriresidues and its application in biobleaching of nonwoody plant pulps"Letters in Applied Microbiology 45 (2007) 467-472.*
PCT, Notification of Transmittal of the International Search Report and the Written Opinion of the International Searching Authority, in Application No. PCT/US14/27242, dated Jul. 7, 2014 (22 pages).
Toren et al. "Emulsifying Activities of Purified Alasan Proteins from Acinetobacter Radioresistens KA53" Applied and Environmental Microbiology, Mar. 2001, pp. 1102-1106 vol. 67, No. 3, Abstract (5 pages).

* cited by examiner

*Primary Examiner* — Nashaat Nashed
(74) *Attorney, Agent, or Firm* — McAndrews Held & Malloy, Ltd.

(57) ABSTRACT

Provided herein are compositions and methods that can remove, metabolize, or degrade a hydrocarbon in an area that is contaminated by hydrocarbons. Methods for bioremediation of an area such as an area of land, a body of water, or a shoreline that are contaminated by a hydrocarbon, such as from a crude oil spill are also described. The compositions and methods described herein can be used on natural flora and fauna as well as manmade materials that are contaminated by a hydrocarbon.

12 Claims, 4 Drawing Sheets

(i)　　　　　　　(ii)　　　　　　　(iii)

FIGURE 1 (con't.)
E 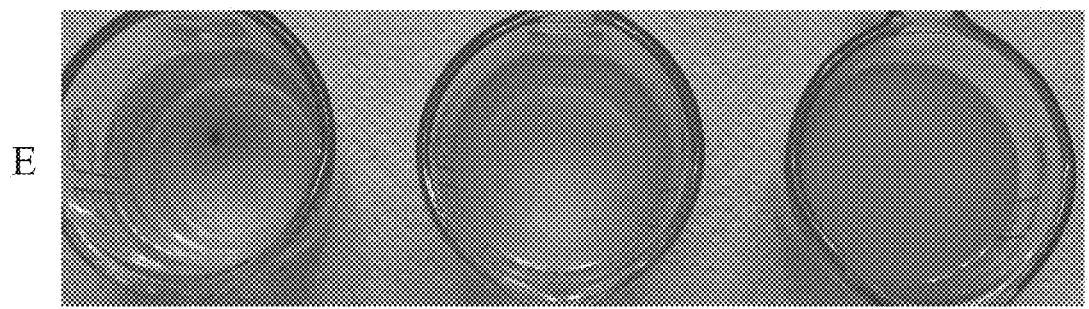
F 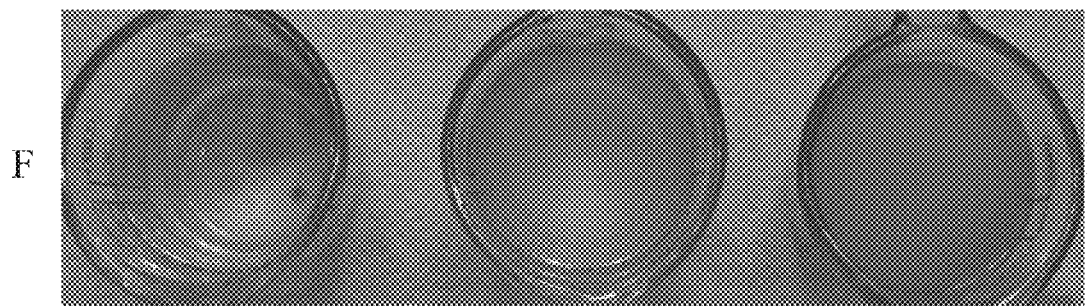
(i)　　　　　　　　(ii)　　　　　　　　(iii)

COMPOSITIONS AND METHODS OF USE

CROSS-REFERENCE TO RELATED APPLICATIONS

This application is related to and claims the benefit of priority to U.S. Provisional Patent Application Ser. No. 61/788,424, filed Mar. 15, 2013, and which is incorporated herein by reference in its entirety.

FIELD

The disclosure relates to the field of environmental microbiology and the removal or bioremediation of hydrocarbon contaminants from the environment. The disclosure relates to compositions that include a mixture of microorganisms, nutritive components, emulsifiers, and enzymes that provide for bioremediation and that are useful in removing, degrading, and/or bioremediation of a hydrocarbon from an area, as well as and methods the incorporate the compositions.

BACKGROUND

Hydrocarbon contamination and oil spills cause significant economic and environmental damage. Crude oil and refined fuel spills have damaged an array of ecosystems ranging from arctic and tundra in Alaska and Russia, to tropical and subtropical regions (e.g., the Gulf of Mexico). While the amount of oil released in an accident is a major factor in estimating the severity of the contamination (e.g., from a few hundred tons to several hundred thousand tons (e.g., Deepwater Horizon Oil Spill, Atlantic Empress, Amoco Cadiz)) it is a combination of the amount of the material and the location of the spill that provides a gauge of the cost of resources and impact on the environment. Smaller spills, such as the Exxon Valdez for example, can have a large impact on an ecosystem because of the remoteness of the site or the difficulty is launching and maintaining an emergency environmental response.

In light of the continuing increase in the demand for energy, oil spills are a persistent risk and consequence of fossil fuel-based energy production. In order to meet the increasing global demand for oil, activities surrounding oil exploration, production, and processing are also likely to increase. This, in turn, increases the opportunities for environmental contamination arising from oil production. Oil spills may result from the release of crude oil (or refined petroleum products (such as gasoline, diesel fuel, kerosene) and their by-product wastes) from tankers, offshore platforms, drilling rigs wells, pipelines, and storage containers or containment vessels. Oil spills are notoriously difficult to contain and clean up in marine areas (e.g., oceans and coastal waters) as well as freshwater rivers and lakes, but spills that occur on land may also be difficult to clean up, and may also pose immediate safety concerns (e.g., due to breakages or spillages associated with storage/containment vessels or transport pipelines, and exposure near population centers). Typically, however, oil spills on land are more readily containable by using techniques such as building makeshift earth dams around the spill site, and land animals can avoid the oil more easily relative to aquatic life. Marine spills are particularly challenging to contain and clean up since they can spread for hundreds of nautical miles in a thin oil slick which can eventually spread to and contaminate beaches with a thin coating of oil, or as agglomerates (e.g., "tar balls"). Oil slicks can kill all varieties of sea life, including sea birds, sea mammals, fish, shellfish and other organisms that it comes in contact with and/or coats.

Cleanup and recovery from an oil spill is difficult and depends upon many factors, including the type of oil spilled, the temperature of the water (affecting evaporation and biodegradation), and the types of shorelines and beaches involved. Spills may take weeks, months or even years to clean up. As such, the existing methods that are used to remove oil contaminants from an ecosystem and for cleaning and restoring the environment are not adequate. For example, there is a huge economic cost for clean-up strategies that strategies that use oil dispersant technology, such as used in the Deep Water Horizon accident. Furthermore using dispersants may dissipate the observable oil slicks, oil agglomerate "chocolate mousse," and tarballs, but they do not remove the oil or contaminating hydrocarbons from the environment. Current research coming from the Gulf waters that were exposed to the Deep Water Horizon accident is showing that chemical dispersants such as Corexit (e.g., Corexit 9527A and 9500A), may combine with crude oil to make it more bioavailable and significantly more toxic to marine organisms, particularly smaller and/or microscopic organisms such as Rotifera. (See, Rico-Martinez, R., et al., Environmental Pollution (February 2013) 173:5-10; epub November 2012). Therefore, not only are the current strategies for containment and clean-up of hydrocarbon contamination extremely expensive, the techniques and reagents used in the existing strategies may be causing more environmental damage and causing more toxicity to native flora and fauna than would the oil on its own.

Accordingly, there is a continuing need for new strategies for lessening or eliminating the prolonged impact of hydrocarbon pollutants, such as those associated with oil production and processing, and that help to restore the exposed environment and contaminated flora and fauna to its natural state.

SUMMARY

In an aspect, the disclosure provides a composition comprising a microbial component; an enzymatic component; an emulsifying component; and a nutritive component. In some embodiments, the composition may further comprise a substrate or carrier component. In embodiments the composition may comprise by weight percent of the total weight of the composition: about 5-75% microbial component; about 5-25% enzymatic component; about 5-20% emulsifying component; and about 5-30% nutritive component. In some embodiments the composition further comprises about 5-30% of a substrate or carrier component. In some embodiments, the composition may further comprise about 5-30% water. In further embodiments, the composition may be an aqueous solution, suspension, dispersion, paste, or slurry, or an emulsion such as, for example, an oil-in-water emulsion.

In some embodiments, the composition may comprise the microbial component from about 10% to about 60% by weight percent. In certain embodiments, the ratio of the amount of the microbial component to the amount of enzymatic component from about 1:1 to about 10:1 (by weight). In some embodiments the ratio of the amount of the microbial component to the amount of combined nutritive and emulsifying components is about 1:1 to about 7:1. In even further embodiments, the composition may comprise the microbial, enzymatic, and combined nutritive and emulsifying components in the relative amounts (by weight) of about 5:1:2.5, respectively.

In some embodiments, the composition comprises a microbial component having at least one microbe that is capable of metabolizing a hydrocarbon component of crude oil. In certain embodiments, the microbial component comprises at least one microbe selected from a bacteria of the genus *Pseudomonas, Achromobacter, Arthrobacter, Bacillus, Lactobacillus, Micrococcus, Nocardia, Vibrio, Acinetobacter, Brevibacterium, Corynebacterium, Flavobacterium, Leucothrix, Rhizobium, Spirillum, Xanthomonas, Alcaligenes, Cytophaga, Thermomicrobium, Klebsiella, Enterobacter, Blastochloris, Thaurea, Azoarcus, Dechloromonas, Geobacter, Desulfobacula, Desulfobacterium*, and *Sphaerotilus*; a yeast of the genus *Candida, Cladosporium, Rhodotorula, Rhodosporidium, Saccharomyces, Sporobolomyces, Trichosporon, Hansenula*, and *Aureobasidium*; a fungus of the genus *Penicillium, Cunninghamella, Verticillium, Beauveria, Mortieriella, Phoma, Scolecobasidium, Tolypocladium, Aspergillus, Graphium, Paecilomyces, Fusarium, Acremonium, Mortierella, Gliocladium, Trichoderma*, and Sphaeropsidales; or an algae selected from the genus *Prototheca, Oscillatoria, Microcoleus, Anabaena, Agmenellum, Coccochloris, Nostoc, Aphanocapsa, Chlorella, Dunaliella, Chlamydomonas, Ulva, Cylindretheca, Amphora, Porphyridium*, and *Petalonia*; or any combination thereof. In some embodiments, the composition comprises at least one microbe selected from the group of *Bacillus licheniformis, Bacillus subtilis, Bacillus amyloliquefaciens, Bacillus pumilus, Pseudomonas putida, Pseudomonas fluororescens, Lactobacillus acidophilus*, and *L. Salivarius bifidum*, or a consortium of microbes comprising at least two, three, four, five, six, seven, or all eight of the above identified microbes.

In further embodiments the composition comprises an emulsifying component that includes lecithin, a fatty acid, glycerol, a glycolipid, a triglyceride, a phospholipid, a cationic surfactant, an anionic surfactant, an amphoteric surfactant, or a non-ionic surfactant. In some embodiments, the emulsifying component may comprise a high or low molecular weight biosurfactant selected from rhamnolipids (*Pseudomonas aerugniosa*), trehalose lipids (*Arthrobacter paraffineus, Rhodococcus erythropolis, Mycobacterium* spp.), sophorose lipids (*Candida lipolytica, Torulopsis bombicola*), viscosin (*Pseudomonas fluorescens*), surfactin (*Bacillus subtilis*), polymixins (*Bacillus polymyxa*), gramicidin S (*Bacillus brevis*), phospholipids (*Acinetobacter* spp., *Thiobacillus thiooxidans*), lipopeptides (*Bacillis pumilis, Bacillus licheniformis, Pseudomonas fluorescens*), polyol lipids (*Rhodotorula glutinis, Rhodotorula graminis*), serrawettin (*Serratia marcescens*), corynomycolic acids, spiculisporic acids (*Corynebacterium lepus, Arthrobacter parafineus, Penicillium spiculisporum, Talaromyces trachyspermus*), sulfonylipids (*Capnocytophaga* spp.), diglycosyl diglycerides (*Lactobacillus fermentii*), alasan (*Acinetobacter radioresistens*), emulsan (*Acinetobacter calcoaceticus*), biodispersan (*Acinetobacter calcoaceticus*), liposan (*Candida lipolytica*), mannan-lipoprotein (*Candida tropicalis*), food emulsifier (*Candida utilis*), insecticide emulsifier (*Pseudomonas tralucida*), sulfated polysaccharide (*Halomonas eurihalina*), and acetyl heteropolysaccharide (*Sphingomonas paucimobilis*). In some embodiments, the emulsifying component comprises lecithin, and an optional biosurfactant that is produced from one or more of the microbes in the microbial component.

In some embodiments, the composition may comprise an enzymatic component including one or more of amylase, lipase, papain, bromelain, cellulase, hemicellulase, protease AO, or pancreatin, or any combination thereof. In some embodiments, the enzymatic component comprises a mixture at least two enzymes selected from amylase, lipase, papain, bromelain, cellulase, hemicellulose, protease AO, and pancreatin.

In some embodiments, the nutritive component comprises spirulina, probiotics, or a complex, minimal, or chemically defined microbial growth medium, or any combinations thereof.

In further embodiments, the composition may further comprise an additional source of nitrogen and phosphate. In other embodiments, the composition may further comprise a substrate component selected from the group consisting of carbon (e.g., activated charcoal), salts, brans, starches, flours, and biodegradable fibers.

In another aspect, the disclosure relates to a method for removing hydrocarbons from an area that is contaminated by hydrocarbons comprising (a) providing an amount of a composition as disclosed herein, and (b) applying an amount of the composition to at least a portion of the area contaminated by hydrocarbons, wherein the applying is performed under conditions that allow for the hydrocarbons to be removed.

In yet another aspect, the disclosure provides a method for promoting bioremediation in an area contaminated by a hydrocarbon comprising (a) providing an amount of a composition as disclosed herein, and (b) applying an amount of the composition to at least a portion of the area contaminated by the hydrocarbon, wherein applying is performed under condition that allow the composition to promote in situ bioremediation.

In a further aspect, the disclosure provides a method for cleaning hydrocarbons from a surface that is contaminated by hydrocarbons comprising (a) providing an amount of a composition as disclosed herein, and (b) applying an amount of the composition to at least a portion of the surface contaminated by hydrocarbons, wherein the applying is performed under conditions that allow for the hydrocarbons to be removed.

In embodiments of the above methods, the contaminated area may be a body of water selected from seawater, fresh water, brackish water, wetland, swamp, or ice. In other embodiments, the contaminated area may be a land mass. In further embodiments, the contaminated area may comprise a natural or man-made solid surface selected from the group consisting of plants, rocks, soils, metals, plastics, rubber, woven fiber, and concrete. In some embodiments the methods relate to cleaning of containers used to hold hydrocarbons such as, for example, oil tanker liners, metal holding drums, refinery holding tanks, waste containment vessels, and the like.

The disclosure provides for other aspects and embodiments that will be apparent to one of skill in the art in light of the following description.

BRIEF DESCRIPTION OF DRAWING

FIG. 1A was taken 10 minutes after the addition of either microbes (ii) or Composition A (iii) to the samples. FIG. 1B was taken on day 3. FIG. 1C was taken on day 5. FIG. 1D was taken on day 7. FIG. 1E was taken on day 10. FIG. 1F was taken on day 12.

FIG. 2A corresponds to the control (salt water+crude oil). FIG. 2B corresponds to microbes (salt water+crude oil+microbes).

FIG. 2C corresponds to an embodiment of the disclosed composition (salt water+crude oil+Composition A).

FIG. 3A corresponds to the control (salt water+crude oil). FIG. 3B corresponds to microbes (salt water+crude oil+microbes). FIG. 3C corresponds to one embodiment of the disclosed composition (salt water+crude oil+Composition A).

DETAILED DESCRIPTION

Figure 1:
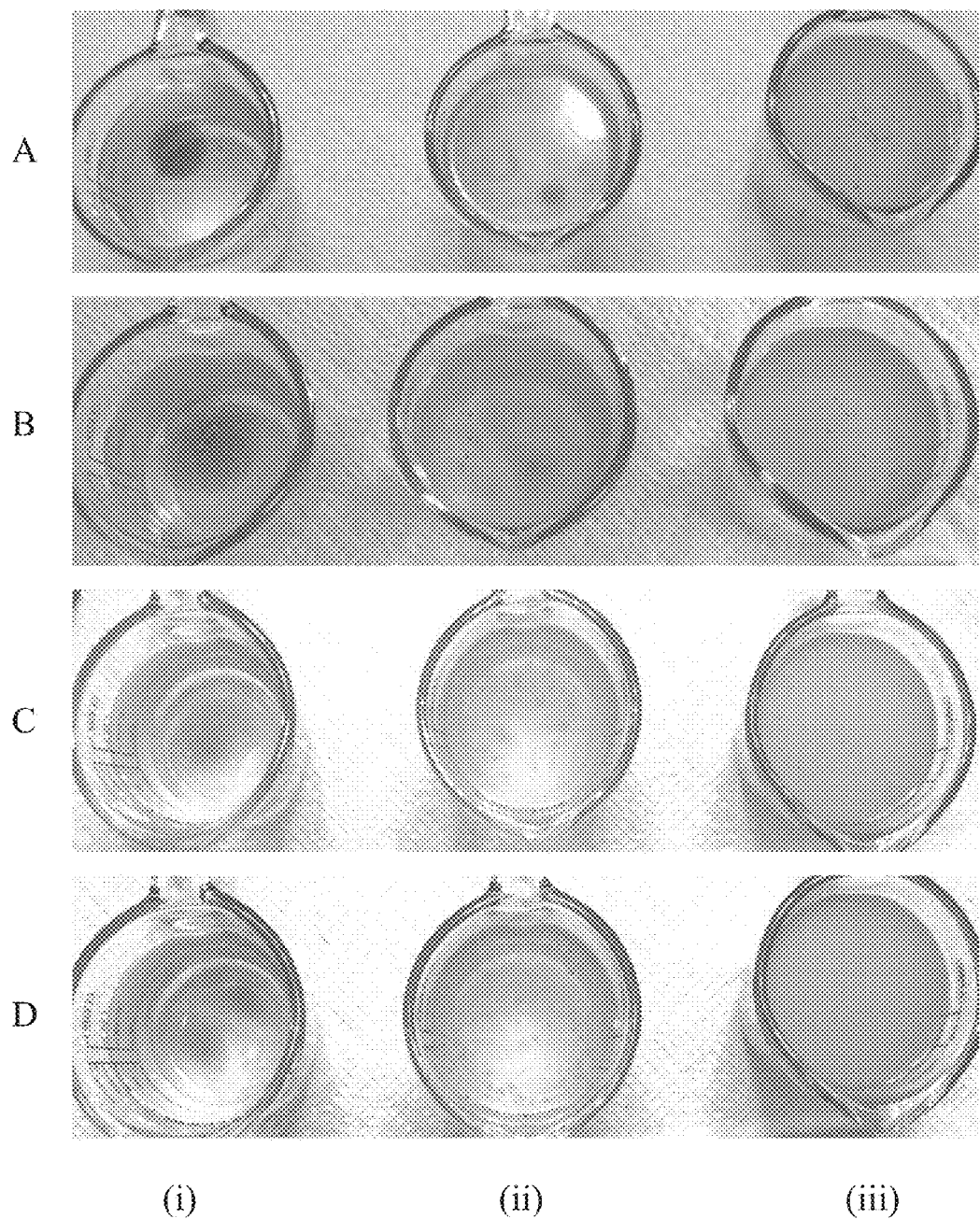
FIG. 1 depicts a series of photographs of three reaction vessels taken over a period of two weeks, where the vessel in column (i) correspond to controls (salt water+crude oil), the vessel in column (ii) correspond to addition of microbes (salt water+crude oil+microbes), and the vessel in column (iii) correspond to an embodiment of the disclosed composition (salt water+crude oil+Composition A).

In a general sense, the disclosure relates to a composition that comprises a blend of microorganisms, enzymes, and nutritive components that are surprisingly effective in processing, metabolizing, and eliminating hydrocarbons upon contact. The inventor has identified that compositions comprising effective combinations of components including microbes, enzymes, emulsifiers, nutritional media, and optional carriers and/or substrates can reduce or eliminate the impact of contaminating hydrocarbons in or on any general location, surface, or environment, or in a particular ecosystem. The composition may be provided in a form that is suitable for application to a body of water, to an area of land, to man-made articles of manufacture, or to a living organism (plant and animal) that has been exposed to and/or has been contaminated with, a substance comprising hydrocarbons. Accordingly, the compositions and methods disclosed herein provide for the elimination of hydrocarbon contamination, or the reduction of the impact of hydrocarbon contamination, and represent a significant improvement upon the existing methods and compositions used to remove contaminant hydrocarbons from an area such as, for example, an ecosystem.

The compositions and methods disclosed herein provide for significant advantages relative to existing strategies for removal of hydrocarbons (e.g., oil spills). Some advantages include avoiding toxicity associated with chemical dispersant and/or detergent compositions, avoiding contact between oil droplets and organisms that live on the ocean floor and in the water column, and restoring or even enhancing the ecological balance of the contaminated ecosystem to the state prior to the contamination. A further advantage provided by the compositions and methods disclosed herein is that they can be used and are effective under adverse weather conditions, strong currents, or regardless of tide patterns that can typically render existing methods of oil removal partially or completely ineffective. The compositions also suitably comprise components that are readily available from a variety of commercial sources and therefore represent a significant cost savings over existing compositions (e.g., chemical dispersants) and methods that are used to abate contamination arising from hydrocarbons.

A particular advantage provided by embodiments of the compositions disclosed herein is that they may be effective in removing or reducing the amount of contaminating hydrocarbon while comprising only components that have no or very low toxicity to plants and animals, and are biodegradable (leaving little to no residue in the environment). To the extent that the composition leaves any residue, it may suitably serve as a nutritional source for the native life in the particular ecosystem. Accordingly, the compositions described herein represent an attractive alternative to other agents used in the management of hydrocarbon contamination, such as chemical dispersants, which are becoming associated with greater regulatory scrutiny and have a more significant impact on the environment.

Other objects, advantages and novel features of the invention will become apparent from the following description and the accompanying drawings.

It should be appreciated, and is discussed in more detail below, that all numerical ranges disclosed herein are intended to include any particular number within that range as well as sub-ranges that fall within the scope of the broader range. For example, a range of 0.01% to 5.0% will be understood to also encompass ranges falling at or above 0.01% and at or below 5.0% (e.g., 3.7%, 1.0%, 0.02%-0.04%, 0.02%-4.5%, 0.05%-4.08%, or 0.03%-1.0%, etc). These are just examples of the types of numbers and ranges that would be encompassed.

All patents and non-patent literature references cited herein are incorporated by reference in their entirety for all purposes.

Hydrocarbons

The compositions and methods disclosed herein provide for the elimination or the reduction of the impact of hydrocarbon contaminants in the environment. The terms "hydrocarbon," "hydrocarbons," "contaminating hydrocarbons" or "hydrocarbon contaminants" as used herein are generally interchangeable and refer to the carbonaceous material that constitutes the majority of crude oil, refined oil, and petroleum products, as described below or otherwise known in the art. In some embodiments, a hydrocarbon comprises oil, crude oil, refined oil, or petroleum products such as, for example, petroleum, alkanes, alkenes, alkynes, aromatics, naphthas, asphaltenes, and the like.

Crude Oil Hydrocarbons

Crude oil comprises a mixture of different hydrocarbons, as well as minor amounts of organic compound containing nitrogen, oxygen, and sulfur, and trace metals (e.g., iron, nickel, copper and vanadium). The exact molecular composition of crude oil varies widely by location to formation. The most common hydrocarbons in crude oil are alkanes (linear or branched), cycloalkanes, aromatic hydrocarbons, and heavier components such as waxes and asphaltenes. The unique mix of molecular components for each crude oil variety defines its physical and chemical properties, such as color and viscosity.

The alkanes, or paraffins, are saturated hydrocarbons with straight or branched chains which contain only carbon and hydrogen and have the general formula $C_nH_{2n+2}$. Although trace amounts of shorter or longer hydrocarbon molecules may be present in crude oil, it generally contains alkanes having from 5 to 40 carbon atoms per molecule, as the $C_{1-4}$ alkanes (i.e., methane, ethane, propane, and butane) are typically in gaseous form under atmospheric conditions. The alkanes from pentane ($C_5H_{12}$) to octane ($C_8H_{18}$) are refined into gasoline, while alkanes from nonane ($C_9H_2O$) to hexadecane ($C_{16}H_{34}$) are refined into diesel fuel, kerosene, and jet fuel. The larger alkanes (e.g., more than 16 carbon atoms) can be refined into fuel oil and lubricating oil, or can be cracked into smaller hydrocarbons and used for higher value products.

The cycloalkane, or naphthene, component includes saturated hydrocarbons with one or more carbocyclic groups of the formula $C_nH_{2n}$. The aromatic hydrocarbons in crude oil are unsaturated hydrocarbons, typically including benzene moieties, of the formula $C_nH_n$.

During the refining process, the different hydrocarbon components are separated by fractional distillation (i.e., by carbon chain length) to produce the particular endproduct(s).

Analysis of Hydrocarbon Content

The amount of various molecules in an oil sample can be determined in laboratory. The molecules are typically extracted in a solvent, then separated in a gas chromatograph, and finally determined with a suitable detector, such as a flame ionization detector or a mass spectrometer. Due to the large number of co-eluted hydrocarbons within oil, many cannot be resolved by traditional gas chromatography and typically appear as a hump in the chromatogram. This unresolved complex mixture (UCM) of hydrocarbons is particularly apparent when analyzing weathered oils and extracts from tissues of organisms exposed to oil. Any of the methods that are known in the art as useful for determining the amount of hydrocarbons in a sample, as well as those that can provide for the compositional analysis of a particular hydrocarbon source may be used in connection with the compositions and methods disclosed herein, such as for example total petroleum hydrocarbon (TPH) analysis, gas chromatography, heavy metal analysis, UV light detection (e.g., Vertek's LVUV ultraviolet LED technologies), or by indirect measurement using assays that identify the presence of one or more component(s) of the compositions disclosed herein (e.g., the 2,6-DCPIP assay for detecting hydrocarbon-degrading bacteria (e.g., Kubota, et al., *Biodegradation* (2008) 19:749-757).

Compositions

In an aspect, the disclosure provides for a composition comprising amounts of a microbial component, an enzymatic component, an emulsifying component, and a nutritive component. In some embodiments, the composition can further comprise a substrate. Suitably, the composition comprises the various components in amounts that are effective to reduce or eliminate the immediate damaging effects of hydrocarbon contamination, and consequently the persistent, long-term damaging effects that are typical of hydrocarbon contamination on an ecosystem. The composition can be applied to an area of land, a body of water, an organism (animal or plant), or a man-made article of manufacture (boats, holding tanks, clothing) in an amount that is effective to degrade hydrocarbons at a rate that is accelerated relative to the natural hydrocarbon biodegradation processes provided by native microbial populations, weathering of hydrocarbons, or typical cleansing protocols. In some aspects, the compositions and methods described herein can provide for the reduction of the amount of contaminating hydrocarbon almost immediately upon application (i.e., within minutes).

The amount of the various components in the composition, including microbes, enzymes, emulsifiers, and nutritional components can range broadly and can depend on the particular type of microbe(s), enzyme(s), emulsifier(s), as well as the intended use of the composition (e.g., based on method of application, the location, and/or particular hydrocarbon contaminant). For example, in some embodiments, the composition can comprise an amount of the microbial component in a range of about 5% to about 75% (by weight percent of the total composition), about 10% to about 60%, about 20% to about 60%, about 30% to about 60%, about 40% to about 60%, about 40% to about 50%, or about 40%, 41%, 42%, 43%, 44%, 45%, 46%, 47%, 48%, 49%, or about 50%. As noted previously herein, the recited weight percent ranges of the components that comprise the composition should be understood to encompass all weight percent values falling within those ranges (e.g., "about 40% to about 50%" includes about 41%, 42%, 43%, 44%, 45%, 46%, 47%, 48%, 49%, and 50% as well as including fractions of those weight percent values (e.g., 45.1%, 45.2%, 45.3%, 45.4%, 45.5%, 45.6%, 45.7%, 45.8%, and 45.9%).

In some embodiments, the composition can comprise an amount of the enzymatic component in a range of about 0.1%-75% (by weight percent of the total composition), 0.1%-70%, 0.1%-65%, 0.1%-60%, 0.1%-55%, 0.1%-50%, 0.1%-45%, 0.1%-40%, or about 0.1% to about 35%, about 1% to about 30%, about 1% to about 25%, about 5% to about 25%, about 5% to about 20%, about 5% to about 15%, about 5% to about 10%, about 10% to about 15%, or about 10%.

In some embodiments, the composition can comprise an amount of the emulsifier component in a range of about 0.1% to about 40% (by weight percent of the total composition), about 1% to about 30%, about 1% to about 25%, about 5% to about 25%, about 5% to about 20%, about 5% to about 15%, about 5% to about 10%, about 10% to about 15%, or about 10%.

In some embodiments, the composition can comprise an amount of the nutritive component in a range of about 0.1% to about 40% (by weight percent of the total composition), about 1% to about 30%, about 1% to about 25%, about 5% to about 25%, about 5% to about 20%, about 5% to about 15%, about 5% to about 10%, about 10% to about 15%, or about 10%.

As noted above, any of the recited weight percent ranges of the component in the composition should be understood to encompass all weight percent values falling within those ranges (e.g., "about 10% to about 15%" includes about 10%, 11%, 12%, 13%, 14%, and 15% as well as including fractions of those weight percent values (e.g., 10.1%, 10.2%, 10.3%, 10.4%, 10.5%, 10.6%, 10.7%, 10.8%, and 10.9%).

While the amount of the various components in the composition may range broadly beyond those embodiments disclosed above, a composition suitably contains amounts of the various components to be effective in reducing the amount of hydrocarbon contaminant. In some embodiments, the amount (e.g., weight %) of microbial, enzyme, emulsifier, and nutritive components in the composition together provide for a composition that meets or exceeds the EPA requirements for a product suitable for certain uses and in certain applications (e.g., sold as a crude oil bioremediation product, such as a powder, lyophilisate, concentrate, or ready-to-use product).

In some embodiments, and as discussed below, the composition can include one or more carriers and/or diluents in addition to the microbial, enzymatic, emulsifier, and nutritive components such as, for example, any solid or liquid carrier or diluent that is commonly used in environmental applications (e.g., agricultural or horticultural compositions). Suitably, any included additional carrier or diluent will not reduce the efficacy of the composition to degrade, metabolize, or otherwise remove the contaminating hydrocarbon, relative to the efficacy of the composition in the absence of the additional component. Suitable carriers and diluents are discussed in more detail below. The composition can include varying amounts of other components such as, for example, surfactants (e.g., non-ionic, anionic, cationic, and zwitterionic surfactants); fatty acids and fatty acid esters (e.g., methyl palmitate/oleate/linoleate); and other auxiliary ingredients such as, for example, emulsifiers, dispersants, stabilizers, suspending agents, penetrants, coloring agents/dyes, and fragrances, as necessary or desired. These optional additional components can be included in the compositions in any amount as long as the composition has some amount of efficacy in removing a contaminating hydrocarbon.

In some embodiments, the disclosure provides a composition comprising, consisting essentially of, or consisting of a microbial component, an enzymatic component, an emulsifier, a nutritive component and an optional substrate carrier. In embodiments, the composition includes the microbial component, the enzymatic component, the emulsifier, and the nutritive component, wherein the amount of microbial component provides from about 100 million to about 100 billion colony forming units (CFU) per gram of combined nutritive component and emulsifier. In some embodiments, the composition includes the microbial component, the enzymatic component, the emulsifier, and the nutritive component, wherein the amount of enzymatic provides from about 500,000 thousand to about 20 million enzymatic units (e.g., digestion units) per gram of combined nutritive component and emulsifier. Suitably, the nutritive component and the emulsifier are provided in about equivalent amounts, but may vary in relative ratios with each other from about 1:5, 1:4, 1:3, 1:2, 1:1, 0.5:1, 0.3:1, 0.25:1, or 0.2:1, or any ratios falling within the ranges of about 1:5 to about 0.2:1.

In certain embodiments, the ratio of the amount of the microbial component to the amount of enzymatic component from at least about 1:1, at least about 2:1, at least about 3:1, at least about 4:1, at least about 5:1, at least about 6:1, at least about 7:1, at least about 8:1, at least about 9:1, or at least about 10:1 (by weight), or any ratios falling within the ranges of at least about 1:1 to about 10:1. In embodiments, the ratio of the enzymatic component to the microbial component may be less than about 1:1, less than about 1:2, less than about 1:3, less than about 1:4, less than about 1:5, less than about 1:6, less than about 1:7, less than about 1:8, less than about 1:9, or less than about 1:10, or less than any ratios falling within the ranges of about 1:1 to about 1:10. In some embodiments the ratio of the amount of the microbial component to the amount of combined nutritive and emulsifying components is about 0.5:1 to about 10:1 by weight (e.g. at least about 1:1, 2:1, 3:1, 4:1, 5:1, 6:1, 7:1, 8:1, 9:1, or at least about 10:1), or any ratios falling within the ranges of at least about 0.5:1 to about 10:1. In embodiments, the ratio of the combined nutritive and emulsifying components to the microbial component may be less than about 1:0.5 (e.g., less than about 1:1, 1:2, 1:3, 1:4, 1:5, 1:6, 1:7, 1:8, 1:9, or less than about 1:10), or any ratios falling within the ranges of less than about 1:0.5 to about 1:10. In even further embodiments, the composition may comprise the microbial, enzymatic, and combined nutritive and emulsifying components are present in the relative amounts (by weight) in a ratio of about 5:1:2.5, respectively, or any variations to that ratio falling wherein any single value ranges within about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or about 25% (i.e., encompassing ratios of, for example, 6:1:2, 4:1.25:2.5, 6:0.75:2, etc.). As one of skill may recognize, variations to the amounts and ratios of the various components of the composition can be made as needed by the particular use, and without affecting the properties of the composition.

Microbes.

As used herein, the terms "microbe," "microbes," "microorganism," "microorganisms," "microbial component," or "microbial consortium," can refer to one or a plurality of microorganisms of the same type, or a mixture of microorganisms. A number of microbes are known to be able to use petroleum hydrocarbons as an energy source, and have been used to degrade contaminant hydrocarbons under certain conditions. The compositions provided by the disclosure may combine at least one microbe that is known to be able to detoxify hydrocarbons and/or metabolize a hydrocarbon as a source of food energy, with other components that are described. In some embodiments the compositions can be formulated to include particular microbes that are endogenous to a specific environment or ecosystem that is to be treated. Such embodiments that include one or more microbes that are indigenous to an environment or an ecosystem are suitably used when the location of an area to be treated with the composition and methods disclosed herein are associated with some variety of environmental extreme. For example, environmental extremes can include cold temperatures (e.g., in artic and subartic oil exploration and transport) high temperatures (e.g., desert), high altitude, high pressure (e.g., deep sea), and the like. In such embodiments, the endogenous microbe(s) can also preferably metabolize or detoxify contaminants that include a hydrocarbon.

Accordingly, the composition can comprise a variety of microorganisms that are capable of metabolizing a hydrocarbon source such as, for example, bacteria, yeasts, fungi, and algae. A variety of these microorganisms have been identified as capable of processing hydrocarbons, including petroleum hydrocarbons (e.g., alkanes, alkenes, cyclic alkanes and alkenes, asphaltenes, polycyclic aromatics, etc.).

Oil-consuming bacteria are known. For example, sulfate-reducing bacteria (SRB) and acid-producing bacteria are anaerobic, while general aerobic bacteria (GAB) are aerobic. These bacteria occur naturally and will act to remove oil from an ecosystem, and their biomass will tend to replace other populations in the food chain.

Non-limiting examples include bacteria species selected from of the genus *Pseudomonas* (e.g., *P. putida, P. oleovorans, P. fluororescens*), *Achromobacter, Arthrobacter, Bacillus* (e.g., *B. licheniformis, B. subtilis, B. amyloliquefaciens, B. pumilus*), *Lactobacillus* (e.g., *L. acidophilus, L. salivarius bifidum*), *Micrococcus, Nocardia, Vibrio, Acinetobacter, Brevibacterium, Corynebacterium, Flavobacterium, Leucothrix, Rhizobium, Spirillum, Xanthomonas, Alcaligenes, Cytophaga, Thermomicrobium, Klebsiella, Enterobacter*, or *Sphaerotilus*.

Examples of yeasts include species from the genus *Candida, Cladosporium, Rhodotorula, Rhodosporidium, Saccharomyces, Sporobolomyces, Trichosporon, Hansenula*, or *Aureobasidium*.

Examples of fungi include species from the genus *Penicillium, Cunninghamella, Verticillium, Beauveria, Mortieriella, Phoma, Scolecobasidium, Tolypocladium, Aspergillus, Graphium, Paecilomyces, Fusarium, Acremonium, Mortierella, Gliocladium, Trichoderma*, or Sphaeropsidales.

Examples of algae include species from the genus *Prototheca, Oscillatoria, Microcoleus, Anabaena, Agmenellum, Coccochloris, Nostoc, Aphanocapsa, Chlorella, Dunaliella, Chlamydomonas, Ulva, Cylindretheca, Amphora, Porphyridium*, and *Petalonia*.

In some embodiments the composition can comprise at least one microbe that is capable of anaerobic hydrocarbon degradation. Such microbes include non-limiting examples such as anoxygenic photoheterotrophic bacterium (*Blastochloris sulfoviridis*), denitrifying bacteria (*Thaurea aromatica, Azoarcus* sp., *Azoarcus tolulyticus, Dechloromonas* sp. *Pseudomonas* sp., *Vibrio* sp., Strain EbN1, Strain HdN1, Strain HxN1, Strain M3, Strain mXyN1, Strain OcN1, Strain PbN1, Strain pCyN1, Strain pCyN2, Strain T3, Strain ToN1), iron ($Fe^{3+}$) reducing bacteria (*Geobacter metallireducens, Geobacter grbiciae*), and sulfate reducing bacteria (*Anaerolinea* spp (Chloriflexi), *Desulfobacula toluolica, Desulfobacterium cetonicum*, Strain AK-01, Strain Hxd3, Strain mXyS 1, Strain NaphS2, Strain oXyS1, Strain Pnd3, Strain PRTOL1, Strain TD3).

Thus, a variety of microbial species may be suitable for use in the compositions disclosed herein. Such microbes include those listed above generally, as well as those that are otherwise known in the art as described, for example, in Atlas, R. M., *Microbiol. Rev.*, (March 1981) 45(1):180-209; Bartha, R., *Microb. Ecol.*, (1986) 12:155-172; Van Hamme, J. D., et al., *Microbiol. Mol. Biol. Rev.*, (December 2003) 67(4): 503-549, and the references cited therein, each of which are hereby incorporated by reference in their entirety.

In some embodiments the composition can comprise at least one microbe that is capable of degrading hydrocarbons at temperatures from about 4° C. to about 20° C., or from about 4° C. to about 10° C. In some embodiments, the microbes can comprise at least one type of oil-consuming bacteria. Such bacteria can include anaerobic or aerobic bacteria. Non-limiting examples of anaerobic bacteria include sulfate-reducing bacteria (SRB) and acid-producing bacteria, while general aerobic bacteria (GAB) are aerobic. These bacteria may occur naturally and in the presence of the compositions disclosed herein may act to remove (or enhance the activity to remove) a contaminating hydrocarbon (e.g., crude oil) from an ecosystem, and their biomass may replace other populations in the food chain.

In some embodiments, the composition comprises at least one microbe selected from a type of bacteria. In some embodiments, the composition comprises at least one microbe selected from a type of yeast. In some embodiments, the composition comprises at least one microbe selected from a type of fungi. In some embodiments, the composition comprises at least one microbe selected from a type of algae. In some embodiments the composition comprises a microbial component that consists essentially of bacteria. In some embodiments the composition comprises a microbial component that consists essentially of bacteria and yeast. In some embodiments the composition comprises a microbial component that consists essentially of bacteria and fungi. In some embodiments the composition comprises a microbial component that consists essentially of bacteria and algae. In some embodiments the composition comprises a microbial component that consists essentially of bacteria, yeast, fungi, and algae. In some embodiments, the composition comprises at least one microbe selected from the group consisting of *Bacillus licheniformis, Bacillus subtilis, Bacillus amyloliquefaciens, Bacillus pumilus, Pseudomonas putida, Pseudomonas fluororescens, Lactobacillus acidophilus*, and *L. Salivarius bifidum*. In some embodiments the composition may comprise at least two, at least three, at least four, at least five, at least six, or at least seven microbes selected from the group consisting of *Bacillus licheniformis, Bacillus subtilis, Bacillus amyloliquefaciens, Bacillus pumilus, Pseudomonas putida, Pseudomonas fluororescens, Lactobacillus acidophilus*, and *L. Salivarius bifidum*. In some embodiments the composition may comprise a consortium of microbes comprising *Bacillus licheniformis, Bacillus subtilis, Bacillus amyloliquefaciens, Bacillus pumilus, Pseudomonas putida, Pseudomonas fluororescens, Lactobacillus acidophilus*, and *L. Salivarius bifidum*. The microbes herein may be obtained from any known commercial source, or may be cultured from the local environment near the location (or a similar type of environment) of a contaminated hydrocarbon to be removed.

Enzymes.

As used herein, the term "enzyme" may include any variety of enzymes known in the art. Suitable enzymes for use in the compositions disclosed herein such as, for example, a protease, may find use and are well known in industrial settings such as in leather manufacture, in detergents and in cleansing, in desizing, or in food processing (cheesemaking, tenderization of meats, and stabilization of beer).

In embodiments, the enzyme may comprise a protease (e.g., rennin, pancreatin, trypsin, and chymotrypsin, pepsin, cathepsin, papain, ficin, bromelain). As will be appreciated by one skilled in the art proteases can have optimal activity under certain pH ranges and can be selected from alkaline proteases (with optimum activity in the pH range of about 7.5 to 13); neutral proteases (with optimum activity in the pH range from 6.0 to 9.0); or acid proteases (with optimum activity in the pH range from 2.0 to 5.0.

In embodiments the enzyme can comprise one or more amylases (endoamylases, exoamylases, alpha-amylases, beta-amylases). In embodiments the enzyme can comprise one or more lipases (carboxyl esterases). In embodiments, the enzyme can comprise one or more cellulase. In yet further embodiments the enzyme can comprise one or more ligninase.

Non-limiting embodiments of enzymes can include one or more enzyme selected from a gamma-aminobutyrotransaminase, an amylase, a cellulase, a collagenase, a glucose oxidase, a glutamic acid decarboxylase, a hemicellulase, an invertase, a catalase, a lipase, a pectinase, a penicillase, a protease, or a streptokinase. Further non-limiting examples include subtilisin, bromelain, papaine, trypsin, chymotrypsin, pancreatin, lysozyme, and combinations thereof. In some embodiments the enzyme comprises at least one of pancreatin (4×), protease AO, hemicellulase, cellulase, bromelain, papain, lipase, and amylase, or any combination thereof. In further embodiments the enzyme comprises a combination of at least two, three, four, five, six, seven, or eight of pancreatin (4×), protease AO, hemicellulase, cellulase, bromelain, papain, lipase, and amylase.

Suitably, the enzymes may be derived from any organism or tissue including, for example from plants, mammalian tissue (e.g., pancreas, liver, etc.), or from microbes (bacillus species, for example, *B. subtilis, B. licheniformis, B. alkalophilus, B. cereus, B. natto, B. vulgatus, B. mycoides*; streptococci; *Streptomyces; aspergillus*). Thus, enzymes may be derived from natural sources, e.g., subtilisin from Bacillius subtilis or from genetically engineered clones, e.g., subtilisin and mutant subtilisins as described in EPO Publication No. 0130756. See also, Wells, J. A., et al. (1983) Nucleic Acids Res., 11, 7911-7915; Yang, M., et al. (1984) J. Bacteriology, 160, 15-21; Estell, D. A., et al. (1985) J. Biological Chemistry, 260, 6518-6521. In particular embodiments, the enzymes may be provided from any number of known commercially available sources. In various embodiments, the enzyme may be added as a liquid or solid (e.g., powder).

Emulsifiers.

As used herein, the term "emulsifying agent," "emulsifier," or "surfactant" can include any surface active agent known in the art. Any emulsifier (surface active agent), or any combination of emulsifiers, can be used as part of the emulsifier component of the compositions described herein. Suitably, the emulsifying agent is selected such that it will not impede or inhibit the life cycle of the microbe(s) present in the microbial component (e.g., does not inhibit the ability of the microbe to proliferate or metabolize/degrade a hydrocarbon). An emulsifier can be added as a component to the compositions disclosed herein either as a separate component, such as a fatty acid, or it can optionally be produced by a microbe that is included in the microbial component, which can be referred to as a "biosurfactant."

Biosurfactants can be classified as either high molecular weight or low molecular weight. Non-limiting examples of low molecular weight biosurfactants include rhamnolipids (*Pseudomonas aerugniosa*), trehalose lipids (*Arthrobacter paraffineus, Rhodococcus erythropolis, Mycobacterium* spp.), sophorose lipids (*Candida lipolytica, Torulopsis bombicola*), viscosin (*Pseudomonas fluorescens*), surfactin (*Bacillus subtilis*), polymixins (*Bacillus polymyxa*), gramicidin S (*Bacillus brevis*), phospholipids (*Acinetobacter* spp., *Thiobacillus thiooxidans*), lipopeptides (*Bacillis pumilis, Bacillus licheniformis, Pseudomonas fluorescens*), polyol lipids (*Rhodotorula glutinis, Rhodotorula graminis*), serrawettin (*Serratia marcescens*), fatty acids such as corynomycolic acids and spiculisporic acids (*Corynebacterium lepus, Arthrobacter parafineus, Penicillium spiculisporum, Talaromyces trachyspermus*), sulfonylipids (*Capnocytophaga* spp.), diglycosyl diglycerides (*Lactobacillus fermentii*). High molecular weight biosurfactants include such non-limiting examples as alas an (*Acinetobacter radioresistens*), emulsan (*Acinetobacter calcoaceticus*), biodispersan (*Acinetobacter calcoaceticus*), liposan (*Candida lipolytica*), mannan-lipoprotein (*Candida tropicalis*), food emulsifier (*Candida utilis*), insecticide emulsifier (*Pseudomonas tralucida*), sulfated polysaccharide (*Halomonas eurihalina*), acetyl heteropolysaccharide (*Sphingomonas paucimobilis*). Further discussion relating to biosurfactants can be found in Van Hamme, J. D., et al., *Microbiol. Mol. Biol. Rev*, December 2003: pp. 503-549; Makkar & Cameotra, J. Ind. Microbiol. Biotechnol., (1998) 20:48-52; Makkar & Cameotra, *J. Ind. Microbiol. Biotechnol.*, (2002) 58:428-434; Desai & Banat, *Microbiol. Mol. Biol. Rev.*, (1997) 61:47-64; Cameotra & Makkar, *Appl. Microbiol. Biotechnol.*, (1998) 50:520-529; Banat, Makkar, and Cameotra, *Appl. Microbiol. Biotechnol.*, (2000) 53:495-508; and Banat, I., *Biores. Technol.*, (1995) 51:1-12, each of which is incorporated herein by reference.

In some embodiments the emulsifier component may include, but not be limited to, a surface active agent such as a non-ionic surfactant, a cationic surfactant, an anionic surfactant, an amphoteric surfactant, or various combinations thereof. Surface-active compounds may be provided as mixtures and suitably exhibit good emulsifying, dispersing and wetting properties. The surfactants listed below are only to be considered as examples, since a number of surfactants that are conventionally used in the art of formulation and suitable in accordance with the disclosure are described in the relevant literature.

Non-limiting examples of non-ionic surfactants include, amides, alkanolamides, amine oxides, block polymers, alkoxylated primary and secondary alcohols and alkylphenols (e.g., ethoxylated alcohols and ethoxylated alkylphenols), alkoxylated fatty esters, sorbitan derivatives, glycerol esters, propoxylated and alkoxylated fatty acids, alcohols, and alkyl phenols, glycol esters, and polymeric polysaccharides, and combinations thereof. Further disclosure regarding nonionic surfactants can be found in the patent and non-patent literature, for example, in U.S. Pat. No. 4,111,855, U.S. Pat. No. 4,865,773, U.S. Pat. No. 3,717,630; U.S. Pat. No. 3,332,880; and U.S. Pat. No. 4,284,435, which are incorporated herein by reference.

Anionic surfactants may include sulfosuccinates and derivatives thereof, sulfates of ethoxylated alcohols, sulfates of alcohols, sulfates of fatty acids, sulfonates and sulfonic acid derivatives, sulfates and sulfonates of alkoxylated alkylphenols, phosphate esters, and polymeric surfactants, and combinations thereof. Suitable anionic surfactants may be water-soluble soaps as well as water-soluble synthetic surfactants. Soaps which are suitable are the alkali metal salts, alkaline earth metal salts and unsubstituted or substituted ammonium salts of higher fatty acids ($C_1O$—$C_{22}$), such as the sodium or potassium salts of oleic or stearic acid, or of natural fatty acid mixtures which can be obtained, for example, from coconut or tall oil; or fatty acid methyltaurinates. Synthetic surfactants may include fatty sulfonates, fatty sulfates, sulfonated benzimidazole derivatives or alkylarylsulfonates. Examples of fatty sulfonates and fatty sulfates include the sodium or calcium salt of lignosulfonic acid, of the dodecylsulfuric ester or of a fatty alcohol sulfate mixture prepared with natural fatty acids. This group also includes the salts of the sulfuric esters and sulfonic acids of fatty alcohol/ethylene oxide adducts. Examples of alkylarylsulfonates are the sodium, calcium or triethanolammonium salts of dodecylbenzenesulfonic acid, of dibutylnaphthalenesulfonic acid or of a naphthalenesulfonic acid/formaldehyde condensate. Also suitable are corresponding phosphates, including salts, or phospholipids.

Non-limiting examples of amphoteric surfactants include betaines and betaine derivatives, amphoteric imadazoline derivatives and fatty amine and fatty amine ethoxylate derivatives, and combinations thereof.

Cationic surfactants may include amine surfactants, including those containing non-quaternary nitrogen, those containing quaternary nitrogen bases, those containing non-nitrogenous bases and combinations thereof. The cationic surfactants may have, as substituents, at least one alkyl radical of 8 to 22 carbon atoms and, as further substituents, lower alkyl, benzyl or lower hydroxyalkyl radicals which may be halogenated. The salts may be in the form of halides, methylsulfates or ethylsulfates. Non-limiting examples include stearyltrimethylammonium chloride and benzyldi(2-chloroethyl)ethylammonium bromide. Additional cationic surfactants are disclosed in U.S. Pat. No. 3,457,109; U.S. Pat. No. 3,222,201; and U.S. Pat. No. 3,222,213, which are hereby incorporated by reference.

A number of suitable surfactants as described above are commercially available from sources including Harcros Chemicals Incorporated, Union Carbide Corporation and Dow Chemical (Midland, Mich.), Shell Chemical Company (Houston, Tex.), The Procter & Gamble Company (Cincinnati, Ohio), and Akzo Nobel (Fort Worth, Tex. and Houston, Tex.).

In some embodiments the emulsifier component includes at least one fatty acid (including any fatty acid derivative) or at least one phospholipid compound. In some embodiments the emulsifier comprises at least one phospholipid. In some embodiments the at least one phospholipid comprises lecithin.

Nutritive Component.

As used herein, the term "nutritive" relates to any compound or component that can be used as a source of nutrition by at least one of the microbes that form part of the microbial component. The nutritive component can be provided in solid (e.g., powders, lyophilisates), liquid (e.g., nutrient broths), or semi-solid gel form (e.g., agar plates, tapioca beads, etc.). In some embodiments the nutritive enables at least one microbe to proliferate under standard growth conditions. In some embodiments the nutritive allows at least one microbe to proliferate under stressed growth conditions (e.g., extremes temperature (arctic or desert), pH, or salinity, low oxygen environment, nutrient-deficient environment). Non-limiting examples of nutritive components include any variety of culture media such as defined media (e.g., minimal media, trace vitamins and elements, carbon and nitrogen sources), undefined (complex) media (e.g., extracts of yeast, beef, soy, mixtures of proteins and/or essential amino acids), selective growth media (mannitol salt agar), transport media, differential media, enriched media, and probiotic powders (e.g., spirulina).

The amount and type of the nutritive component can be selected based on the composition of the microbial components, or the intended use or location of the composition (e.g., use in methods for removing hydrocarbons in a nutrient sparse environment). In some embodiments, the nutritive component comprises a probiotic composition. In some embodiments, the nutritive component comprises a complex medium. In some embodiments the nutritive comprises spirulina. In some embodiments the nutritive comprises spirulina and a fertilizer.

In some embodiments, the compositions as well as the individual components (e.g., emulsifiers, nutrients, etc.) disclosed herein may include salts, and are preferably selected from pharmaceutically, veterinary or agriculturally acceptable salts. Such acceptable salts are well known in the art and can include, for example, salts of acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids. Basic salts include, but are not limited to, those formed with pharmaceutically acceptable cations, such as sodium, potassium, lithium, calcium, magnesium, ammonium and alkylammonium. Basic nitrogen-containing groups may be quarternised with such agents as lower alkyl halide, such as methyl, ethyl, propyl, and butyl chlorides, bromides and iodides; dialkyl sulfates like dimethyl and diethyl sulfate, and others.

Optional Components

The compositions disclosed herein can further comprise additional components that can help stabilize the composition or provide additional optional features, depending on the particular use or method comprising the composition. Additional ingredients can include, but are not limited to, a pH control agent, such as an acid, a base, or a combination thereof. Acids can suitably include dilute mineral acids or organic acids. Bases can include an alkaline metal salt, or dilute solutions thereof. Additional ingredients also include metal chelating agents (e.g., EDTA, NTA, and polyphosphates), dispersants (e.g., acrylic acid homopolymers, polymers of acrylic and maleic acids, and oil dispersants such as Corexit), fragrance or odor counteractants (e.g., cyclodextrins), hydrotropes (e.g., sodium xylene sulfonate, sodium toluene sulfonate, and sodium cumene sulfonate), additional water miscible solvents, and viscosity modifiers (e.g., natural gums such as guar and synthetic poilymeric resins such as carboxy methyl cellulose and Carbopol brand polymers).

In some embodiments, the composition further comprise a suitable substrate or solid carriers that can be used to provide for compositions to be formulated as dusts and dispersible powders including, for example, salts, plant-derived carriers (cellulose, bran, etc.), ground natural minerals (e.g., calcite, talc, kaolin, montmorillonite or attapulgite), silicas, absorptive polymers, any of which may optionally have high dispersion characteristics. Suitable particulate adsorptive carriers can include porous carriers such as carbon (e.g., activated charcoal), pumice, brick grit, sepiolite or bentonite. Suitable non-absorptive carrier materials include calcite or sand. In some embodiments, any variety of granulated materials of inorganic or organic matter can be used such as, for example, mineral salts or plant materials (fiber residues, celluloses, starches, brans, and the like). In some embodiments, the substrate may comprise carbon (e.g., activated charcoal), salts, brans, starches, flours, or biodegradable fibers.

The compositions may comprise an amount of solvent. Examples of optional solvents include, but are not limited to acids, non-hydrogenated or partially hydrogenated aromatic hydrocarbons, aliphatic or cyclo aliphatic hydrocarbons such as paraffins or cyclohexane, alcohols such as methanol, ethanol, propanol or butanol, glycols and their ethers and esters such as propylene glycol, dipropylene glycol ether, hexylene glycol, ethylene glycol, diethoxy glycol, ethylene glycol monomethyl ether or ethylene glycol monoethyl ether, ketones such as cyclohexanone, isophorone or diacetone alcohol, strongly polar solvents such as N-methylpyrrolid-2-one, N-methyl-pyrrolidine, dimethyl sulfoxide or N,N-dimethylformamide, water, free or epoxidized oils such as, for example, rapeseed oil, castor oil, coconut oil, wintergreen oil, cedarwood oil, rosemary oil, peppermint oil, geraniol, rose oil, palmarosa oil, citronella oil, citrus oils (e.g., lemon, lime, and orange), dillweed oil, corn oil, sesame oil, soybean oil, palm oil, vegetable oil, olive oil, peanut oil, canola oil, and silicone oils.

The compositions may comprise an amount of a fertilizer composition. Suitably, the fertilizer component may supplement the nutritive component of the composition and may be particularly advantageous to include when the intended use of the composition will be under high stress growth conditions for the microbes in the microbial component (e.g., low oxygen, low temperature conditions). Such suitable fertilizer compositions are well known in the art, and typically comprise one or more sources of nutrient nitrogen, phosphorous, oxygen, carbon, or trace minerals and vitamins that are important in promoting microbial growth. In some embodiments, suitable fertilizer compositions comprise a source of nitrogen and phosphorus. The amount of any fertilizer included in the composition can be readily determined by one of skill in the art, given the intended use of the composition, and any particular composition of fertilizer.

Embodiments include commercially useful formulations or "ready-to-use" application forms. In such formulations, the composition can be suitably provided as a mixture with other active compounds, for example, various additional fertilizers, fragrances, carriers and/or delivery vehicles that expand the applicability of the composition described herein. Embodiments provide for the compositions manufactured as formulations that are useful for bioremediation of a crude oil spill. In some embodiments, the composition can be formulated as an emulsion, a liquid concentrate, a sol gel (flowable agent), a spray, an aerosol, or the like, by any standard or conventional methods for mixing and manufacturing such formulations such as, for example, admixing the various agents optionally with any suitable additional inert ingredient that is used as a carrier, solvent, diluent, emulsifier, dispersant, stabilizers suspending agent, or penetrant. The addition of these materials would depend on the active ingredient and the type of formulation and how it is intended to be applied.

Methods for Preparation

The compositions described herein can be generally prepared by any appropriate manufacturing methods and processes and using any appropriate manufacturing equipment such as is known in the art. Suitably, the compositions can be prepared by combining the various components (e.g., microbe(s), enzyme(s), emulsifier(s), nutritive(s), and optional substrate) in an appropriate vessel (considering vessel size, amount of composition to be made and reactivity of components) with mixing (e.g., stirring or shaking) until a uniform or homogeneous composition is achieved. The various composition components can be added sequentially, with mixing between each addition to ensure homogeneous dispersion of the previous component. For example, a composition can be prepared by first adding the one or more microbes of the microbial component to a mixing vessel, adding the nutritive component to the microbial component with stirring or shaking until the components form a homogeneous dispersion. This may be followed by addition of the additional components (e.g., enzyme component, and emulsifier component) with stirring or shaking to provide a homogeneous composition. The optional substrate can be mixed with the homogeneous composition. In some embodiments, the method of manufacture can incorporate sterile methods (e.g., sterilized mixing and storage vessels).

Methods

In an aspect, the disclosure relates to a method for removing hydrocarbons from an area that is contaminated by hydrocarbons comprising (a) providing an amount of a composition as disclosed herein, and (b) applying an amount of the composition to at least a portion of the area contaminated by hydrocarbons, wherein the applying is performed under conditions that allow for the hydrocarbons to be removed.

In yet another aspect, the disclosure provides a method for promoting bioremediation in an area contaminated by a hydrocarbon comprising (a) providing an amount of a composition as disclosed herein, and (b) applying an amount of the composition to at least a portion of the area contaminated by the hydrocarbon, wherein applying is performed under condition that allow the composition to promote in situ bioremediation.

In a further aspect, the disclosure provides a method for cleaning hydrocarbons from a surface that is contaminated by hydrocarbons comprising (a) providing an amount of a composition as disclosed herein, and (b) applying an amount of the composition to at least a portion of the surface contaminated by hydrocarbons, wherein the applying is performed under conditions that allow for the hydrocarbons to be removed.

In embodiments of the above methods, the contaminated area may be a body of water selected from seawater, fresh water, brackish water, wetland, swamp, or ice. In other embodiments, the contaminated area may be a land mass. In further embodiments, the contaminated area may comprise a natural or man-made solid surface selected from the group consisting of plants, rocks, soils, metals, plastics, rubber, woven fiber, and concrete.

According to embodiments of the methods, the composition can be applied to or contacted with the hydrocarbon, or the area surrounding a hydrocarbon contamination, using any suitable delivery method or delivery device. One of skill in the art will appreciate that suitable methods and devices may vary widely, and depend upon any number of factors, including the location of the site of contamination, as well as whether the composition is to be applied to flora or fauna (such as plants, grasses, trees, marine animals, terrestrial animals, birds, amphibians, etc.), applied broadly or specifically to various ecosystems or environments exposed to a contaminating hydrocarbon (rocks, fabrics (e.g., clothing, tank liners), hydrocarbon holding tanks, pipelines, tank liners (e.g., plastics), bodies of water and/or shorelines (e.g., surfaces of marine or freshwater, or within a particular depth the water column, including lake bottoms and seafloor), applied in a particular climate (e.g., arctic or sub-arctic climates, arid climates, tropical or sub-tropical climates), as well as depending on the nature and type of contaminating hydrocarbon (e.g., lighter alkanes, heavy asphaltenes, etc.).

For example, the composition may be applied to areas of hydrocarbon contaminated land or water using any suitable and well known method such as, the manual or automated spreading of dispersible powders, spraying solutions or liquid dispersion, and the like.

Suitable methods for contacting animals contaminated with a hydrocarbon, include, but are not limited to, direct topical application, such as by dipping, scrubbing, or spraying. Where the composition is applied to animals, including humans, formulations suitable for topical application include but are not limited to sprays, aerosols, solutions, scrubs, shampoos, pastes, gels, mousses, creams, and lotions. Similarly, in embodiments wherein the composition is applied to plants directly or indirectly (e.g., over contaminated regions that include plants), suitable application formulations include, but are not limited to, dusts including wettable powders, wettable granules, suspension concentrates, pellets, and liquids including emulsions (e.g., microemulsions), sprays, and aerosols.

Suitably, when composition is used to treat an animal, including a human, that is contaminated with a hydrocarbon the hair or skin of the animal is contacted with the composition, preferably in the region(s) that are contaminated. As noted above, the composition may be applied topically in the form of ointments, aqueous compositions including solutions and suspensions, creams, lotions, aerosol sprays or dusting powders. Animals that may be treated by the methods and compositions disclosed herein can include animals exposed to a contaminating hydrocarbon such as, for example, any of land mammals such as humans, sheep, bears, cattle, horses, pigs, dogs, and cats; birds of any type (e.g., poultry, coastal seabirds, and penguins); marine mammals such as whales, dolphins, porpoises, manatees, seals, sea lions, otters, and walruses; fish; corals; and crustaceans. In embodiments, the methods can incorporate direct application of the composition to the animal (e.g., as a scrub, gel, lotion, dust, etc.), or the indirect application of the composition to the animal (e.g., contacting the water or land in which the animal is present with the composition).

As used throughout the disclosure the term "effective amount" means a concentration of the composition that is sufficient to at least reduce the amount of contaminating hydrocarbon on an animal, plant, or surface of an object, or in an environment relative to the amount of contaminating hydrocarbon in the absence of the composition (or prior to the application of the composition). In some embodiments, an effective amount can remove substantially all the contaminating hydrocarbon. The effective amount of a composition used in the methods described herein may vary depending on the various components of the composition (e.g., types and amounts of microbes in the microbial component, type and amount of emulsifier in the emulsifier component, etc.), the location of the hydrocarbon contamination, and the type and amount of hydrocarbon contamination. Beyond the guidelines provided herein regarding effective amounts, one of skill in the art will be able to determine effective amounts given consideration of the factors discussed above.

As used herein "reducing" when used in connection with methods for "reducing hydrocarbon contaminants," for example, means that the method removes or ameliorates an amount of the hydrocarbon from the area or surrounding area to which the composition is applied. As will be appreciated, the method need not entirely eliminate the contaminating hydrocarbon, and the efficacy of the method may be determined by a qualitative assessment of the area (e.g., a visual assessment) or a quantitative assessment of the area (e.g., using any appropriate analytical technique known in the art). In some embodiments, the method is effective to reduce or substantially reduce the amount of contaminating hydrocarbon. "Substantially reduce" used in connection with amounts of contaminating hydrocarbon can mean that a qualitative assessment (e.g., by appearance of the area of contamination) of the improvement in the reduction of the amount of hydrocarbon contamination arising from the method is at least about 50% to about 100% (e.g., at least about 50%, 55%, 60%, 65%, 70%, 75%, 80%, 85%, 90%, 95%, 96%, 97%, 98%, 99%, or 100%). Thus, in some embodiments, the method can essentially eliminate the amount of hydrocarbon relative to the original amount of contaminating hydrocarbon. In embodiments, the method can reduce the duration of the hydrocarbon contamination (i.e., the time required to remove, reduce, or substantially reduce the amount of contaminating hydrocarbon) at least about 10%, 15%, 20%, 25%, 30%, 35%, 40%, 45%, 50%, 55%, 60%, 65%, 70%, 75%, or more. Accordingly, the methods provided herein can reduce the time it would have taken in the absence of the composition to eliminate or reduce the amount of contaminating hydrocarbon on the order of hours, days, weeks, or months.

In some embodiments, an effective amount of the composition is applied directly to area of hydrocarbon contamination, allowing for direct contact with the hydrocarbon. The composition is left in contact with the contaminated area, or in direct contact with the hydrocarbon, for a period of time that allows for reduction in the amount of the contaminating hydrocarbon. While the period of time will vary depending on the particular location of the contaminated area, under moderate environmental conditions (e.g., air temperatures between 35-110° F., water temperatures between 35-90° F.), the period of time can be from 5 to 180 minutes (e.g., 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 minutes). In other embodiments, the period of time can be on the order of hours such as, for example 1-48 hours (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours). In other embodiments the period of time can be on the order of days such as, for example 1-60 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days).

As noted above, the composition can be applied in effective amounts that are either based on qualitative or quantitative evaluation. For example, in some embodiments, the composition can be applied in an amount ranging in a ratio from about 0.00001:1 to about 100,000:1 (by weight), or from about 0.00001:1, 0.0001:1, 0.001:1, 0.01:1, 0.1:1, 1:1, 10:1, 100:1, 1000:1, 10,000:1, or from about 100,000:1 based on a calculated or an estimated amount of contaminating hydrocarbon or crude oil in an area to be treated. Alternatively, in some embodiments, the composition can be applied in an amount that is effective to cover all or a portion of the surface of a contaminated area, or all or a portion of the observable surface of the contaminating hydrocarbon (e.g., as a slick on the surface of water, or as agglomerated tar balls or "chocolate mousse" in a body of water or on land, etc.). Embodiments of the methods that comprise the qualitative application of the composition may be more convenient when, for example, the particular amount of contaminating hydrocarbon cannot be readily or conveniently determined. As discussed herein, some of the advantages provided by the compositions disclosed herein include that the components comprising the composition are relatively low cost (relative to existing compositions used to reduce hydrocarbon contamination), and that the components can be selected to include components of the natural ecosystem, providing an eco-friendly solution to hydrocarbon removal/decontamination. As such, these advantages in particular can allow for the liberal application and use of the compositions, without being driven by concerns regarding cost, or further environmental contamination by applying amounts of the composition beyond the minimum amount required to be an "effective amount."

As noted above, the effective amount of the composition may depend on any number of factors including the various components used in the composition, the site of hydrocarbon contamination, and the type of hydrocarbon contamination. However, in some embodiments that comprise the use of the composition to remove, decontaminate, or bioremediate hydrocarbons in the form of crude oil, the composition can be suitably applied in amounts that range from about 0.0001:1, 0.001:1, 0.01:1, 0.1:1, 1:1, 10:1, 100:1, 1000:1, or about 10,000:1 (composition:hydrocarbon, by calculated or estimated weight). In some embodiments, these suitable amounts of the composition are applied to crude oil contamination on a body of water. In some embodiments, the body of water is a freshwater lake or river. In some embodiments the body of water is seawater.

In other embodiments, suitable effective amounts of the composition are applied to crude oil contamination on a land mass. In such embodiments, the composition can be suitably applied in amounts that range 0.001:1, 0.01:1, 0.1:1, 1:1, 10:1, 100:1, or about 1000:1 (composition:hydrocarbon, by calculated or estimated weight). Methods that incorporate the application of the compositions to areas of land can further comprise optional additional steps, such as tilling in order to promote mixture and/or penetration of the composition beyond the surface of the land mass, application of oxygenating agents, application of fertilizers, and the like, in order to promote the general health and growth of the microbe(s) in the microbial component of the composition.

The disclosure also provides for use of the methods and compositions described herein in combination with other methods (concurrent or successive) or compositions or active agents that are useful in removing contaminating hydrocarbons (e.g., chemical or physical degradation including, for example, dispersants; physical isolation/separation of hydrocarbons, etc.), or that are able to metabolize and/or bioremediate a hydrocarbon (e.g., alternative microbial formulations).

Thus, in some embodiments of the aspects disclosed herein that relate to methods for cleaning or removing hydrocarbon contaminants from an area, the methods can incorporate additional steps and techniques that currently find use in the containment and removal of hydrocarbons. As discussed above, existing methods for the cleanup and recovery from hydrocarbon contamination, such as from an oil spill, is expensive and unpredictable because its success depends on any number of variables that are location specific. Such factors can include the type and source of the oil or refined hydrocarbon product, or by-product that is spilled as well as the site and climate temperature at the location of the spill. Such factors can have an effect on the physical properties of hydrocarbon (viscosity/flow rate, evaporation rate, etc.) as well as the rate of any biodegradation that might be expected to occur naturally.

Accordingly, in some embodiments the methods disclosed herein can further incorporate existing strategies for hydrocarbon contaminant removal (e.g., oil spill clean-up). Such strategies are generally known in the art, and can be selected by one of skill based on the need or potential need of the use of a removal strategy in addition to the use of the compositions disclosed herein. Additional strategies can include any one or more of the following non-limiting examples.

A bioremediation accelerator may be added, which typically comprises one or more hydrophobic chemical agent(s), and does not contain a microbe. The bioremediation accelerator typically contains components that can interact physically or chemically bond to soluble and insoluble hydrocarbons, and further contains a source of nutrients that can boost the proliferation of indigenous bacteria that can metabolize hydrocarbons. While the accelerators can be used either on land or water, because they generally act as an accumulating agent, accelerators are typically used in the water column and on the surface, and form gel-like agglomerates that float on the water surface.

Chemical dispersants (e.g., typically chemical polymers with or without surface-active or non-surface active polymers) can be used to dissipate oil slicks and are typically added to improve the separation of suspensions or colloids, and preventing settling or agglomeration. Dispersants break up oil slicks that form on surface water through the formation of micelles that transfer and disperse within the water column. This acts to spread the oil throughout a larger volume of water which may aid in avoiding further damage to shorelines, or increase the rate of natural weathering processes. Examples of known and widely used dispersants include Corexit 9527A and 9500A (Nalco, Naperville, Ill.). As noted herein, however, ongoing research implies that dispersants can increase hydrocarbon levels in fish by a factor about 100 and may kill fish eggs. Further, as the dispersant/oil droplets pass into the water column, they can contaminate the sea floor, and can be toxic to coral and microscopic sea life. Accordingly, methods that incorporate the compositions disclosed herein, when used in combination with agents such as chemical dispersants may allow for reductions in the amount agents required for effective removal of contaminating hydrocarbons, and lessen any deleterious effects on the environment.

The vacuum and centrifuge technique can be used advantageously on bodies of water. The technique comprises vacuuming a mixture of water and contaminating oil/hydrocarbon into a holding tank and separating the oil and water by centrifugation. This can allow for recovery of high purity oil fractions, but is typically inefficient because of regulations that prohibit the release of the resulting water fraction because of residual oil contaminants.

Other techniques that may be used to recover or remove hydrocarbon contaminants on bodies of water include dredging (for oil components or oil dispersions more dense than water), skimming (typically requiring calm water), solidifying (oil adsorbent/absorbent polymers that form semi-solid materials), and controlled burning (as an initial step to reduce large amounts of oil in water, and is typically considered under low wind conditions).

The exemplary techniques discussed above are generally known in the art. Further one of skill in the art will be familiar and/or recognize the equipment that may be used in connection with these techniques including, for example, booms, floating barriers, skimmers, sorbents, vacuums, shovels, and the various chemical and biological agents routinely employed in these techniques.

The Examples that follow are intended to be merely illustrative of the aspects and embodiments described above and should not be viewed as limiting to the scope of the appended claims.

EXAMPLES

Materials and Methods

The various components that were used in the non-limiting examples below were obtained from the source as indicated below.

Microbes:

*Bacillus licheniformis, Bacillus subtilis, Bacillus amyloliquefaciens, Bacillus pumilus, Pseudomonas putida, Pseudomonas fluororescens* were each supplied at 10 billion CFU/gram from Microbial Discovery Group, Franklin Wis. *Lactobacillus acidophilus* and *Salivarius bifidum* (were supplied by Danisco, Inc., Madison, Wis.).

Enzymes:

Abbreviations for various unit of enzymatic activity used throughout the disclosure are as follows, unless specifically indicated otherwise: United States Pharmacopeia (USP units) which can be found in the Food Chemicals Codex (2012 Food Chemicals Codex (8th Edition). The United States Pharmacopeial Convention is accessible at the U.S. Pharmacopeial Convention website; Milk Clot Units (e.g., MCU/mg); Casein Digestion Units (e.g., CDU/mg); Papain Unit (e.g., PU); Bromelain Tryosine Units (e.g., BTU/g); Rorer units; Gelatin Digesting Units (e.g., GDU/g). Protocols for determining activity in terms of these units are generally known in the art.

The enzyme components Pancreatin (4×), Protease AO, Hemicellulase, Cellulase, Bromelain, Papain, Lipase, and Amylase were purchased from Bio-Cat (Troy, Va.).

Emulsifiers/Nutritives:

Powdered lecithin granules were purchased from American Lecithin Company, Inc., (Oxford, Conn.). Hawaiian Spirulina powder was purchased from Nutrex Hawaii Inc., (Kailua-Kona, Hi.). The purified water incorporated into the composition mixture was sourced from Cobalt Distribution Co., (Montrose, Calif.).

Substrate:

Bran was purchased from Arrowhead Mills, The Hain Celestial Group (Boulder, Colo.). Sea salt was purchased from wholesale or retail suppliers.

Crude oil was obtained from the U.S. Environmental Protection Agency (EPA) as Alaskan North Slope medium weight crude oil (ANS521) National Environmental Technical Applications Center for Bioremediation Product Evaluation from the University of Pittsburgh Applied Research Center (Pittsburgh, Pa.). Analysis of the composition of the crude oil by gas chromatography-mass spectrometry (GC-MS) is summarized in Table 1.

TABLE 1

CG-MS Analysis of ANS521 Alaskan crude oil

| Alkane/Cycloalkane Hydrocarbons | Amount (µg/g) | Polycyclic Aromatic Hydrocarbons | Amount (mg/g) |
|---|---|---|---|
| C10 | 4.33 | nap | 1.00 |
| C11 | 2.67 | C1-nap | 9.67 |
| C12 | 2.00 | C2-nap | 595.00 |
| C13 | 5.67 | C3-nap | 3124.67 |
| C14 | 268.67 | C4-nap | 2669.33 |
| C15 | 2,511.67 | phe | 430.00 |
| C16 | 3,977.67 | C1-phe | 1295.33 |
| C17 | 4,377.00 | C2-phe | 1767.00 |
| pristane | 2,817.33 | C3-phe | 1481.33 |
| C18 | 4,264.00 | C4-phe | 699.33 |
| phytane | 2,468.00 | flu | 112.33 |
| C19 | 4,021.00 | C1-flu | 476.00 |
| C20 | 3,614.00 | C2-flu | 675.33 |
| C21 | 3,075.00 | C3-flu | 785.00 |
| C22 | 3,372.67 | dbt | 372.33 |
| C23 | 3,189.00 | C1-dbt | 760.00 |
| C24 | 3,009.67 | C2-dbt | 931.33 |
| C25 | 2,920.00 | C3-dbt | 838.33 |
| C26 | 2,699.67 | nbt | 72.67 |
| C27 | 1,994.00 | C1-nbt | 269.67 |
| C28 | 3,333.00 | C2-nbt | 361.67 |
| C29 | 1,485.00 | C3-nbt | 305.67 |
| C30 | 1,051.33 | flt | 4.00 |
| C31 | 891.67 | pyr | 18.67 |
| C32 | 701.00 | C1-pyr | 150.33 |
| C33 | 640.67 | C2-pyr | 0.00 |
| C34 | 769.67 | cry | 95.00 |
| C35 | 901.00 | C1-cry | 194.67 |
|  |  | C2-cry | 256.33 |

TABLE 1-continued

CG-MS Analysis of ANS521 Alaskan crude oil

| Alkane/Cycloalkane Hydrocarbons | Amount (μg/g) | Polycyclic Aromatic Hydrocarbons | Amount (mg/g) |
|---|---|---|---|
| | | C3-cry | 182.33 |
| | | C4-cry | 197.67 |
| Total Alkanes | 58,367.33 | Total Aromatics | 19,132.00 |

Methods.

The test methodology used in some of the Examples was modeled to be compliant with EPA testing procedures for bioremediation products.

Example 1

Composition

An exemplary composition (Composition A) was prepared in order to provide for evaluation of the efficacy in degrading hydrocarbon contaminants, such as those commonly found in crude oil (e.g., heavy crude oil, light crude oil, etc.). Briefly, the composition included a mixture of components including: a microbial component, an enzymatic component, an emulsifying and nutritive component, and an optional substrate. Table 2, identifies the amounts of all the components included in exemplary Composition A.

TABLE 2

Composition A

| | Amount |
|---|---|
| Microbial Components | |
| Bacillus licheniformis | ⅛ tsp. |
| Bacillus subtilis | ⅛ tsp. |
| Bacillus amyloliquefaciens | ⅛ tsp. |
| Bacillus pumilus | ⅛ tsp. |
| Pseudomonas putida | ⅛ tsp. |
| Pseudomonas fluororescens | ⅛ tsp. |
| Lactobacillus acidophilus | ⅛ tsp. |
| L. Salivarius bifidum | ⅛ tsp. |
| Enzymatic Components | |
| Pancreatin (4x) Amylase (20,000 USP) Protease (20,000 USP) Lipase (1,600 USP) | 125 mg |
| Protease AO (5,000 HUT) | 50 mg |
| Hemicellulase (3,000 DU) | 100 mg |
| Cellulase (3,000 DU) | 175 mg |
| Bromelain (3,000 DU) | 175 mg |
| Papain (3,000 DU) | 175 mg |
| Lipase (3,000 DU) | 100 mg |
| Amylase (3,000 DU) | 100 mg |
| Nutritive Components | |
| Powdered lecithin granules (emulsifier) | ¼ tsp. |
| Spirulan Hawaiian powder (nutritional medium) | ⅛ tsp. |
| Substrate Component[1] | |
| Bran | — |
| Sea Salt | — |
| Water | ⅛ tsp. (to aid mixing of dry comp.) |

[1]For the experiments described below, the substrate was varied between bran (Example 3, "freshwater contamination") and sea salt (Examples 2, 3 ("marine contamination"), and 4).

The enzymatic component was premixed using the relative amounts of the enzymes described Table 2. Briefly, at room temperature the individual microbial components were measured and added to a sealable container. The nutritive component and about 1 gram total weight of the enzymatic component were added to the microbial component. The substrate and water were then added to the container. The container was sealed and the composition was mixed by shaking for about 1-2 minutes, or until the mixture appeared homogeneous. The mixture can be stored in a tightly sealed container for a prolonged period of time (months) at room temperature.

Example 2

Degradation of Crude Oil

A series of experiments were conducted to evaluate the efficacy of Composition A, prepared as described in Example 1 (sea salt as substrate), in degrading an aqueous sample contaminated with crude oil. A series of three 1 liter reaction vessels were filled with about 100 mL of salt water solution (sea water, from Instant Ocean Aquarium Systems, Mentor, Ohio). The solutions were allowed to equilibrate to room temperature (~72 F) for 12 hr. Following temperature equilibration, solution pH was measured to be about 7.8. A uniform amount of Alaskan crude oil (0.5 g) was gently added to the center of each of the three vessels using a sterilized Pasteur pipette. One of the reaction vessels was maintained as a control and contained only salt water and crude oil.

An amount of a mixture containing only the microbes (i.e., about 0.25 g-0.5 g of the mixture including ⅛ tsp. of each of the microbes in the "microbial component" in Table 2) was added to the second vessel. Composition A (about 0.25 g-0.5 g) was added to the third reaction vessel. After addition of the microbes and Composition A, all the reaction vessels were swirled to mix and simulate gentle, brief wave action. The reaction vessels were maintained in open air at room temperature for a period of 14 days, and gently agitated by swirling once a day. Photographs of the reaction vessels were taken each day under normal lighting conditions and under exposure to a black light source. See, FIGS. 1-3.

Results

Figure 2:
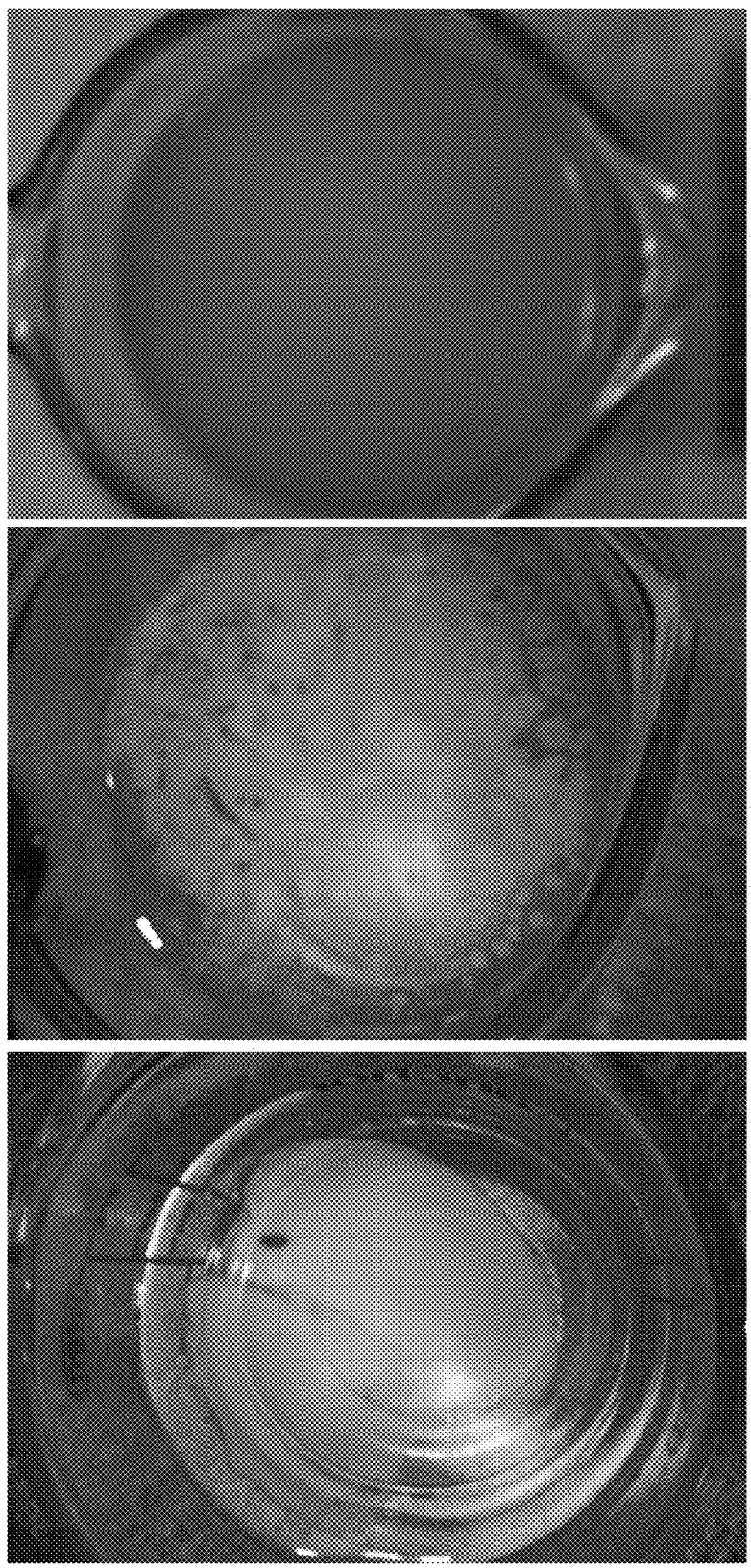
FIG. 2 depicts the same three reaction vessels with photographs taken on day 7 upon exposure to a black light.

The addition of Composition A to the reaction vessel had a striking and immediate effect on the appearance of the oil slick. FIG. 1 depicts a series of photographs of the three reaction vessels taken over a period of two weeks, where the vessels in column (i) correspond to controls (salt water+crude oil), the vessels in column (ii) correspond to addition of microbes (salt water+crude oil+microbes), and the vessels in column (iii) correspond to addition of Composition A (salt water+crude oil+Composition A). FIG. 1A was taken 10 minutes after the addition of the microbes (ii) and Composition A (iii) to the samples. Surprisingly, even within 10 minutes of addition, Composition A began to process and break down the crude oil, forming small punctate bodies having the appearance of ground pepper. While Composition A effectively dispersed the oil slick, the oil slick was still evident in both the control and microbes sample (appearing as dark blotches as swirls in FIG. 1A(i) and (ii)).

By day 7 the sample containing Composition A was completely clear and homogeneous in appearance, where even the small punctate bodies that had formed almost immediately upon contact could no longer be observed by visual inspection (FIG. 1D (iii)). While the oil slick was less pronounced on day 7 in each of the control and microbes samples relative to its appearance on days 1 and 3, it was still easily identified by visual inspection (FIGS. 1B-1D). Over the course of the entire 14 day experiment, the oil slick was still observable as dark blotches and swirls in the control and microbes samples (FIGS. 1E-1F on days 10 and 12, respectively).

Figure 3:
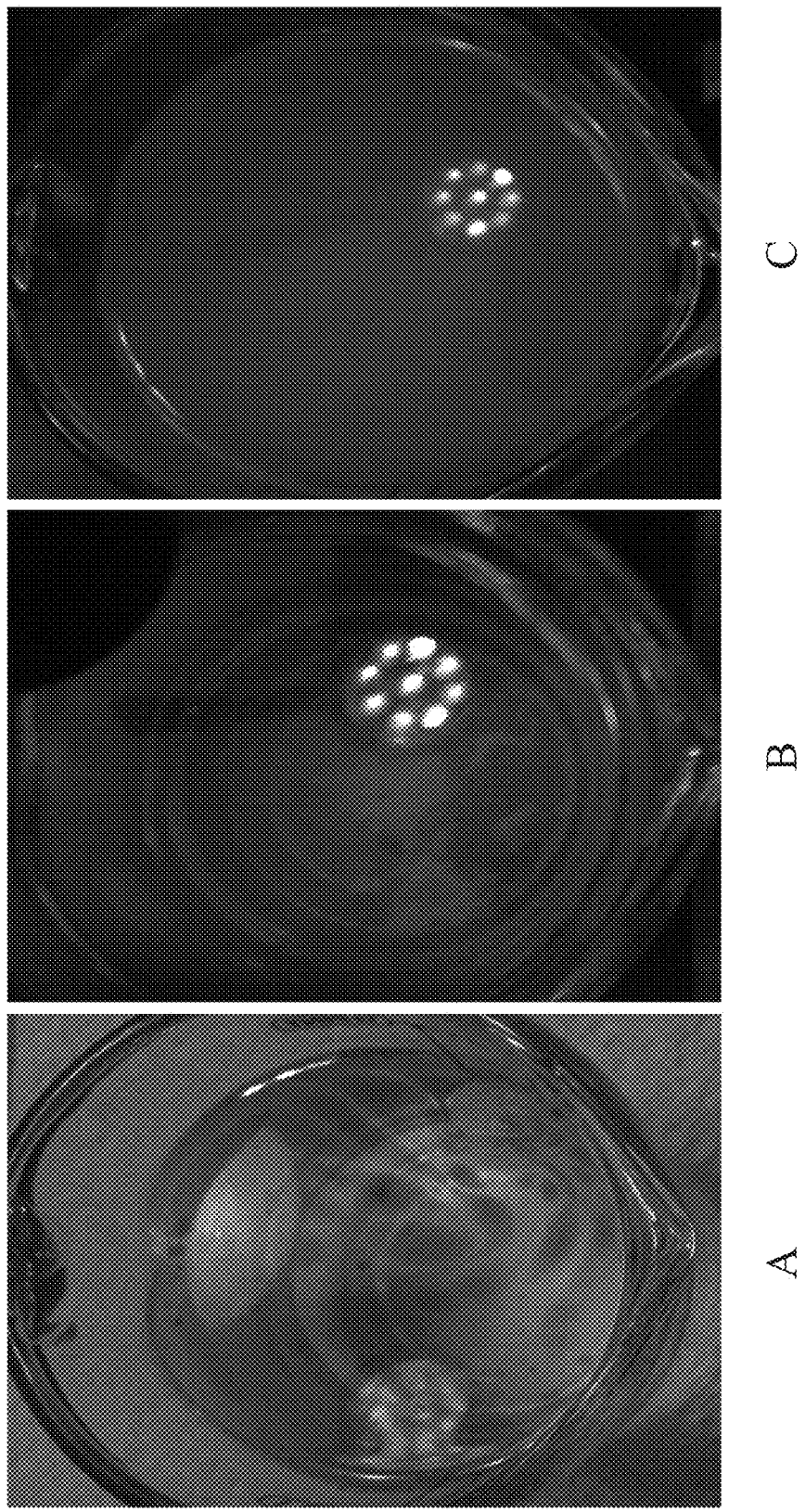
FIG. 3 depicts photographs upon exposure to a black light of the same three reaction vessels of FIGS. 1 & 2 that were taken on day 12.

Under a black light source on day 7, the oil slick was easily observed in the control and microbes only samples (FIGS. 2A, 2B, splotchy, light gray regions), while there was no evidence of any oil in the sample containing Composition A (FIG. 2C, homogeneous appearance). FIG. 3 depicts the samples under black light on day 12. While the black light itself is seen as a reflection in the figure (patterned white circles in 3B, 3C), even at day 12 the control and microbes samples retained an amount of oil slick (non-homogeneous regions in FIGS. 3A, 3B), relative to the sample with Composition A (FIG. 3C, homogeneous appearance).

This experiment demonstrates that compositions disclosed herein, as exemplified by Composition A, are not only more effective than a composition containing only microbes or just standard weathering in dispersing and decomposing contaminating crude oil in a simulated marine environment, but that the compositions are unexpectedly fast and effective in dispersing and decomposing crude oil. As depicted in FIG. 1A, within 10 minutes of contacting an oil slick with Composition A, the oil slick itself was completely dispersed and appears as small flocculent or punctate moieties. Over the course of days 2-7, the composition was effective in returning the salt water sample to its original appearance, having eliminated even the small, dark particulates from the sample. These results are particularly surprising—and encouraging—because the general samples were left to sit generally still over the course of the experiment, with only gentle swirling of the vessels once per day. It is generally recognized that oxygenation and wave action help to disperse and dissipate oil slicks by increasing the rate of oil weathering and promote conditions that are more favorable endogeneous microbes that may be able to metabolize oil. As such, the compositions described herein are not only effective in oxygen-rich environments, but also in low oxygen environments.

Example 3

Bioremediation of Water

Field tests were performed using the composition according to Example 1 in order to observe its effects and potential for remediation of large bodies of fresh water and seawater contaminated with crude oil.

Marine Contamination.

In July 2010, the inventor visited the coastal waters of Barataria Bay, near Grand Isle, La., which was effected by the Deepwater Horizon oil spill disaster. As documented at the time of the disaster, the recovery strategy employed the use of the oil dispersant Corexit. Since the time of that disaster, chemical dispersants such as Corexit have received intense scrutiny, with a number of researches concluding that the use of chemical dispersants to manage oil spills in marine or freshwater ecosystems may be cause more damage to the ecosystem than the crude oil itself. Recent reports have even linked these dispersants with health problems in people who have been exposed to them, reporting incidences of seizures, difficulty with movement, blindness, and even suicide.

The inventor prepared several containers of Composition A (Example 1) and applied it to smaller areas where crude oil slicks had collected, as well as to rocky areas that had been exposed to oil. Upon contacting the contaminated water with Composition A, a surface channeling action was observable. After just several minutes of contact, the surface area of the water that had been contacted with the composition appeared to have a normal appearance and was easily distinguishable from the areas that had not been contacted where oil slick was still observable.

Freshwater Contamination.

In August of 2010, the inventor visited a 25 mile region of the Kalamazoo River that had been contaminated by a rupture in the Enbridge Energy, which was estimated to spill over 1 million gallons of heavy crude oil into the environment. As of the summer of 2012, the total cost associated with clean up the spill was about $765 million. While most of the river was reopened by the end of June 2012, some sections of the river remain closed or restricted to the public.

Again, the inventor prepared several containers of Composition A, with bran instead of salt as the substrate as the contamination was a body of freshwater, and applied it to smaller areas of the river water where crude oil slicks were clearly visible. As the waters of the river were much less turbulent than the waters in the Gulf coast, very pronounced channeling action on the water surface was observable upon contact with Composition A. Within minutes of its application Composition A clarified the areas of surface water it contacted, with immediately adjacent regions still retaining a dirty appearance caused by the oil slick.

While the results of these initial small-scale field tests are qualitative they demonstrate that the compositions described herein are able to dissipate the appearance of oil slicks on fresh and salt water surfaces, returning the surface to a more natural appearance.

Example 4

Assessment of Effect on Marine Wildlife

Additional testing was performed to assess the efficacy and impact that Composition A has on remediating a simulated marine microsystem (with marine wild life) was conducted following the qualitative oil spill field tests performed in the Gulf of Mexico and in the Kalamazoo River (Example 3). An amount of crude oil (0.5 g) was added to about 100-200 mL of a saltwater solution (sea water from Instant Ocean Aquariums) in a small fish tank. Composition A (about 0.25 g-0.5 g) was added to the contaminated fish tank. The mixture was occasionally mixed by gentle swirling (the tank was not equipped with a filter). As detailed in Example 2, the action of Composition A in dispersing and eliminating the crude oil slick was immediately visible. Seven days after adding Composition A to the contaminated fish tank, any crude oil that was visible appeared as very small punctate bodies. At this time, a male Siamese fighting fish, or "betta" fish (*Betta splendens*), was introduced to the tank. After a brief initial equilibration period, the betta fish appeared to show no signs of stress and was swimming naturally. The fish was fed according to a normal schedule and has continued to thrive in the tank for well over two years.

Example 5

Bioremediation of Soil

As Examples 2-4 demonstrate, the compositions disclosed herein are effective in remediating the environment of contaminating hydrocarbons by dissipating and removing crude oil in marine and freshwater ecosystems. The compositions described herein are also expected to be equally surprisingly effective in dissipating and remediating crude oil and hydrocarbon contamination on land and on surfaces. The compositions described herein, such as the exemplary Composition A described in Examples 1-4, will be tested in controlled experiments to assess its ability to biodegrade hydrocarbons on natural and manmade solid surfaces such as, for example, plants, rocks, soils, metals/alloys, plastics, rubber, woven fiber, and concrete.

For example, small samples (e.g., 15-100 g) of soils (e.g., garden soil, topsoil, subsoil, etc.), rocks (e.g., sand, gravel, river rock, concrete, etc.), plastics (e.g., materials used as internal liners for oil tankers), and metals (e.g., steel) will be exposed to an amount of a contaminating hydrocarbon source, such as crude oil. An amount of a composition as disclosed herein will be applied to the contaminated samples using methods that are appropriate based on the sample type. For example, either a solution or solid powder composition may be conveniently added to soil samples, while solutions, slurries, or pastes comprising the composition may be more convenient to apply to samples comprising rock, plastics, or metal materials, as well as to indigenous flora and/or fauna (e.g., as a wash, spray, solution, rinse, gel, lotion, paste, shampoo, or scrub). Contaminated control samples will also be maintained under conditions that are identical to the test samples, but without the application or addition of the composition.

After a period of days following the initial application on soil, for example, the effect of the composition will be evaluated by any qualitative or quantitative techniques that are commonly used in the art. The data and results from the study will be evaluated in order to determine whether the content, amount, or mode of administration of the composition has any effect on the results of the remediation of the contaminating hydrocarbons.

It is expected that samples that are treated with a composition comprising the compositions disclosed herein, whether used alone or in combination with another method or composition effective for removing or remediating hydrocarbons or crude oil contamination will exhibit more rapid processing of the contaminating hydrocarbon relative to samples that are not contacted with the composition. It is further expected that using the compositions described herein in combination with another existing method or composition for dissipating or removing a contaminating hydrocarbon will reduce either the duration of the other method or the amount of the other composition by a significant amount. As such, the compositions and methods described herein provide for a more rapid removal of contaminating hydrocarbons and reduce the costs associated with current methods of hydrocarbon remediation.

I claim:

1. A composition comprising a microbial component, an enzymatic component, an emulsifying component, and a nutritive component, wherein
    the microbial component comprises about 5-75% of the total weight of the composition and comprises an equal amount by weight of *Bacillus licheniformis, Bacillus subtilis, Bacillus amyloliquefaciens, Bacillus pumilus, Pseudomonas putida, Pseudomonas fluorescens, Lactobacillus acidophilus*, and *L. Salivarius bifidum;*
    the enzymatic component comprises about 5-25% of the total weight of the composition and comprises by weight about 10-15% pancreatin (4x); about 3-7% protease AO; about 10-15% hemicellulase, about 15-20% bromelain, about 15-20% papain, about 10-15% lipase, and about 10-15% amylase;
    the emulsifier component comprises about 5-20% of the total weight of the composition and comprises (by weight) about 5-15% lecithin; and
    the nutritive component comprises about 5-30% of the total weight of the composition and comprises by weight about 3-10% spirulan.

2. The composition of claim 1, further comprising (by weight) about 3-10% water, and a substrate selected from the group consisting of bran and sea salt.

3. The composition of claim 2, wherein the composition consists of:
    a microbial component comprising an equal amount by weight of *Bacillus licheniformis, Bacillus subtilis, Bacillus amyloliquefaciens, Bacillus pumilus, Pseudomonas putida, Pseudomonas fluorescens, Lactobacillus acidophilus*, and *L. Salivarius bifidum;*
    an enzymatic component comprising by weight about 10-15% pancreatin (4x); about 3-7% protease AO; about 10-15% hemicellulase, about 15-20% bromelain, about 15-20% papain, about 10-15% lipase, and about 10-15% amylase;
    an emulsifier component comprising by weight about 5-15% lecithin;
    a nutritive component comprising by weight about 3-10% spirulan;
    about 3-10% water; and
    a substrate selected from the group consisting of bran and sea salt.

4. The composition of claim 3, wherein
    the microbial component consists of an equal amount by weight of *Bacillus licheniformis, Bacillus subtilis, Bacillus amyloliquefaciens, Bacillus pumilus, Pseudomonas putida, Pseudomonas fluorescens, Lactobacillus acidophilus*, and *L. Salivarius bifidum;*
    the enzymatic component consists of by weight about 10-15% pancreatin (4x); about 3-7% protease AO; about 10-15% hemicellulase, about 15-20% bromelain, about 15-20% papain, about 10-15% lipase, and about 10-15% amylase;
    the emulsifier component consists of by weight about 5-15% lecithin; and
    the nutritive component consists of by weight about 3-10% spirulan.

5. The composition of claim 1, wherein the composition further comprises about 5-30% of a substrate component.

6. The composition of claim 5, wherein the substrate component is selected from the group consisting of activated charcoal, salts, brans, starches, flours, and biodegradable fibers.

7. The composition of claim 1, wherein the composition further comprises about 5-30% water.

8. The composition of claim 1, wherein the microbial, enzymatic, and combined nutritive and emulsifying components are present in the relative amounts by weight of about 5:1:2.5, respectively.

9. The composition of claim 1, wherein the nutritive component further comprises an additional source of nitrogen and phosphate.

10. A method for removing hydrocarbons from an area that is contaminated by hydrocarbons comprising:
    (a) providing an amount of the composition according to claim 1;
    (b) applying an amount of the composition to at least a portion of the area contaminated by hydrocarbons, wherein the applying is performed under conditions that allow for the hydrocarbons to be removed.

11. The method of claim 10, wherein the contaminated area is a body of water selected from seawater, fresh water, brackish water, wetland, swamp, or ice.

12. The method of claim 10, wherein the contaminated area is a land mass.

\* \* \* \* \*